Figure 1:
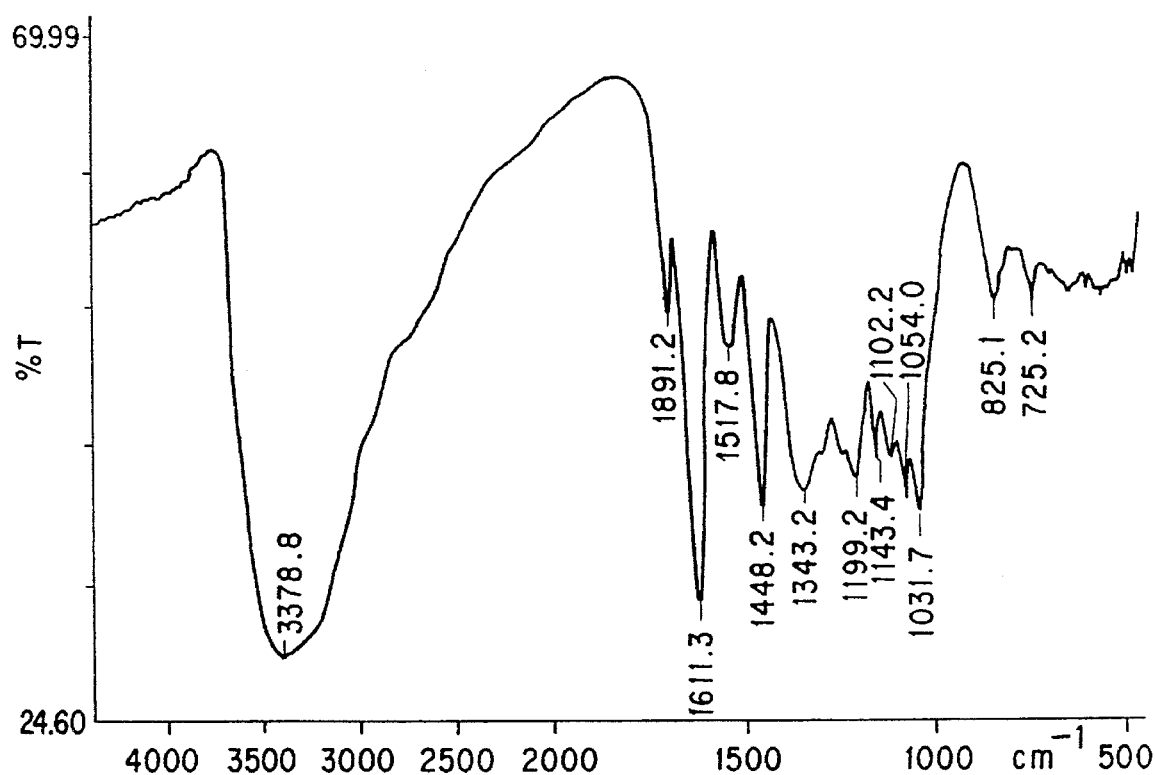

United States Patent [19]
Tempesta

[11] Patent Number: 5,494,661
[45] Date of Patent: Feb. 27, 1996

[54] METHODS FOR USING PROANTHOCYANIDIN POLYMERS HAVING ANTIVIRAL ACTIVITY

[75] Inventor: Michael S. Tempesta, Moss Beach, Calif.

[73] Assignee: Shaman Pharmaceuticals, Inc., South San Francisco, Calif.

[21] Appl. No.: 194,779

[22] Filed: Feb. 9, 1994

Related U.S. Application Data

[60] Continuation of Ser. No. 916,311, Jul. 17, 1992, abandoned, which is a division of Ser. No. 737,077, Jul. 29, 1991, Pat. No. 5,211,944, which is a continuation-in-part of Ser. No. 596,893, Oct. 12, 1990, abandoned.

[51] Int. Cl.$^6$ .......................... A01N 65/00; A61K 31/765
[52] U.S. Cl. ..................... 424/78.38; 424/195.1
[58] Field of Search ............................. 424/78.01, 195.1, 424/78.38

[56] References Cited

U.S. PATENT DOCUMENTS

| | | | |
|---|---|---|---|
| 4,698,360 | 10/1987 | Masquelier | 514/456 |
| 4,806,659 | 2/1989 | Itsuo et al. | |
| 4,863,956 | 9/1989 | Gabetta et al. | 514/453 |
| 4,925,871 | 5/1990 | Gabetta et al. | 514/453 |

FOREIGN PATENT DOCUMENTS

| | | |
|---|---|---|
| 1086651 | 9/1980 | Canada . |
| 0025649 | 8/1980 | European Pat. Off. . |
| 2407910 | 11/1974 | Germany . |
| 59-196884 | 11/1984 | Japan . |
| 62-048677 | 3/1987 | Japan . |
| WO/90/04968 | 5/1990 | WIPO . |
| WO90/13304 | 11/1990 | WIPO . |

OTHER PUBLICATIONS

Rao—Indian J. of Plant Physiology vol. XXIX, No. 3, 1986 pp. 278–280.
Foo et al Phytochem. of . . . Polymers 1980 vol. 19 pp. 1747–1754.
Newman et al Mag. Resonance in Chemistry, vol. 25, 118–124 (1987).
Vaisberg et al. Planta Medica 55 1989 pp. 141–143.
Beladi et al Ann. N.Y. Acad. Sic. 1977 (284) pp. 358–364.
Delcour et al., 1983, Chem. Soc. Perkin Trans. 1:1711–17.
Czochanska, et al. 1979, J.C.S. Chem. Comm. 375–77.
Jones et al., 1978, Physiochemistry 15:1407–09.
Mattice and Porter, 1984, Phytochemistry 23:1309–11.
Porter et al., 1982, J.C.S. Perkin 1:1217–21.
Thompson et al., 1972, J.C.S. Perkin 1:1387–99.
Hemingway et al., 1982, J.C.S. Perkin 1:1209–16.
Fletcher et al., J.C.S. Perkin 1:1628–37.
Morimoto et al., 1986, Chem. Pharm. Bull. 34:633–42.
Gujer et al., 1986, Physiochemistry 25: 1431–36.
Bettolo and Scarpati, 1979, Phytochemistry, 18:520.
Pieters et al., 1990, Phytochemistry, 29(1):348–349.
Perdue et al., 1979, J. Pharm. Sci., 68:124–25.
McManus et al., 1981, J.C.S. Chem. Comm., 309–11.
Englund et al., 1988, Ann. Int. Med., 1:203–08.
Edwin Haslam, in *Plant Polyphenols—Vegetable Tannins Revisited*, Cambridge University Press, New York, ch. 2 pp. 14–89, Pranthocyanidins.
Misra and Dixit, 1983, Ind. J. Pharm. Sci., 216–19.
Cai et al., 1991, Phytochemistry, 30:2033–40.
G. Wayne McGraw, "Reactions at the A–Ring of Proanthocyanidins" in Chemistry and Significance of Condensed Tannins, Hemingway and Karchesy eds., Plenum Press, New York, pp. 227–283.

(List continued on next page.)

*Primary Examiner*—Peter F. Kulkosky
*Attorney, Agent, or Firm*—Pennie & Edmonds

[57] ABSTRACT

The present invention provides for proanthocyanidin polymers with significant antiviral activity. The proanthocyanidin polymers can be chemically synthesized or can be isolated from a Croton or a Calophyllum plant species. The present invention encompasses methods of using proanthocyanidin polymers in treating warm-blooded animals, including humans, infected with a respiratory virus.

22 Claims, 18 Drawing Sheets

OTHER PUBLICATIONS

Richard W. Hemingway, "Structural Variations in Proanthocyanidins and Their Derivatives" in Chemistry and Significance of Condensed Tannins, Hemingway and Karchesy eds., Plenum Press, New York, pp. 83–107.

Peter E. Laks, "Condensed Tannins as a Source of Novel Biocides" in Chemistry and Significance of Condensed Tannins, Hemingway and Karchesy eds., Plenum Press, New York, pp. 503–515.

Czochanska et al., 1980, J.C.S. Perkin, 1:2278–86.

Lawrence J. Porter, "Flavans and Proanthocyanidins" in The Flavonoids, J. B. Harborne, ed., Chapman and Hall, New York, pp. 21–62.

J. W. T. Selway, "Antiviral Activity of Flavones and Flavans" in Plant Flavonoids in Biology and Medicine: Biochemical Pharmacological and Structure–Activity Relationship, Alan R. Liss, Inc., 1986, pp. 521–536.

Roux et al., Biochem. J. 82:320–324 (1962).

Konowalchuk et al., J. Food Science 41:1013–1017 (1976).

Konowalchuk et al., Appl. Environ. Microbiol., 32(6):757–763 (1976).

Konowalchuk et al., Appl. Environ. Microbiol. 36(6):798–801 (1978).

Konowalchuk et al., Appl. Environ. Microbiol. 35(6):1219–1220 (1978).

Takechi et al., Phytochem. 24(10):2245–2250 (1985).

Spencer et al., Phytochemistry 27(8):2397–2409 (1988).

Fukuchi et al., Antiviral Res. 11:285–298 (1989).

Scholz and Rimpler, Planta Medica 55:379 (1989).

PPA* = PROANTHOCYANIDIN POLYMER A

PPA* = PROANTHOCYANIDIN POLYMER A

METHODS FOR USING PROANTHOCYANIDIN POLYMERS HAVING ANTIVIRAL ACTIVITY

CROSS-REFERENCE TO RELATED APPLICATION

This is a continuation of application Ser. No. 07/916,311, filed Jul. 17, 1992, now abandoned, which in turn is a division of application Ser. No. 07/737,077 filed Jul. 29, 1991, now U.S. Pat. No. 5,211,944, which in turn is a continuation-in-part of application Ser. No. 07/596,893 filed Oct. 12, 1990, which is incorporated herein by reference and is now abandoned.

1. FIELD OF THE INVENTION

The present invention relates to the use of proanthocyanidin polymers, having 2 to 30 flavonoid units, in treating respiratory virus infections. Additionally, it has been found that the use of the proanthocyanidin polymers having 6 to 30 flavonoid units is effective in treating virus infections in general. The chemical characteristics of certain newly discovered proanthocyanidin polymers are also encompassed.

2. BACKGROUND OF THE INVENTION

2.1 ETHNOBOTANICAL USES OF EXTRACTS FROM THE CROTON TREE AND FROM CALOPHYLLUM INOPHYLUM

A number of different Croton tree species, including *Croton salutaris, Croton gossypifolius, Croton palanostima, Croton lechleri, Croton erythrochilus* and *Croton draconoides*, found in South America, produce a red viscous latex sap called Sangre de Drago. It is most often utilized by mixed descent and native people of the Peruvian Amazon for flu and diarrhea. It is taken internally for tonsillitis, throat infections, tuberculosis, peptic ulcers, intestinal disorders, rheumatism and to enhance fertility and is used by both adults and children. It is also used extensively to stop bleeding, herpes, and for wound healing. The sap is placed directly on open wounds as an anti-infective and to accelerate the healing process. It is applied to the gums of patients after tooth extractions. It is also utilized as a vaginal wash in cases of excessive bleeding.

It has been shown that Sangre de Drago from *Croton draconoides* and from *Croton lechleri* contains an alkaloid identified as taspine, which exhibits anti-inflammatory activity, Persinos et al., 1979, *J. Pharm. Sci.*, 68:124. Taspine has also been shown to inhibit RNA-directed DNA polymerase activity in the myeloblastosis virus, Rauscher leukemia virus and Simian sarcoma virus (Sethi, 1977, *Canadian J. Pharm. Sci.*, 12:7).

*Calophyllum inophylum* is a tree ranging from India to East Africa to Polynesia. Seed oil is used in folk medicine as an antiparasitic in treatment of scabies, ringworm and dermatosis as well as other uses such as for analgesia. In Indo-China the powdered resin is used for ulcers and wound healing. In Indonesia the bark is applied externally to treat swollen glands and internally as a diuretic. The sap is used as an emollient for chest pain as well as for tumors and swelling. Leaf extracts are used as a wash for inflamed eyes. The Cambodians use leaf extracts in inhalations for treatment of vertigo and migraine. The Samoans use the sap as an arrow poison.

2.2 PROANTHOCYANIDIN MONOMERS AND POLYMERS AND THEIR USES ;

Proanthocyanidin and proanthocyanidin polymers are found as colorless phenolic substances in a wide variety of many plants, particularly those with a woody habit of growth (e.g., the Croton species and *Calophyllum inophylum*). The general chemical structure of a polymeric proanthocyanidin consists of linear chains of 5, 7, 3', 4' tetrahydroxy or 5, 7, 3', 4', 5' pentahydroxy flavonoid 3-ol units linked together through common C(4)–(6) and/or C(4)–C(8) bonds, as shown below.

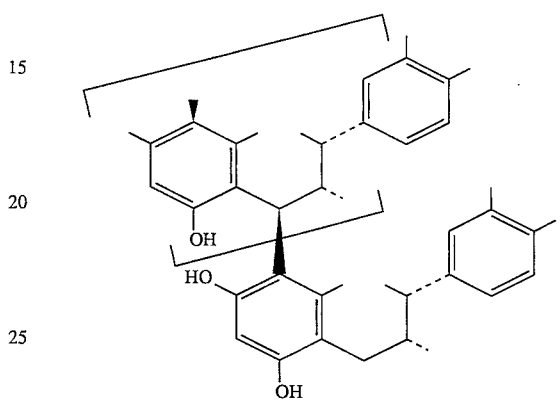

Biosynthetic studies have indicated that proanthocyanidin polymers consist of monomer units of the type shown below, See Fletcher et al., 1977, *J.C.S. Perkin*, 1:1628.

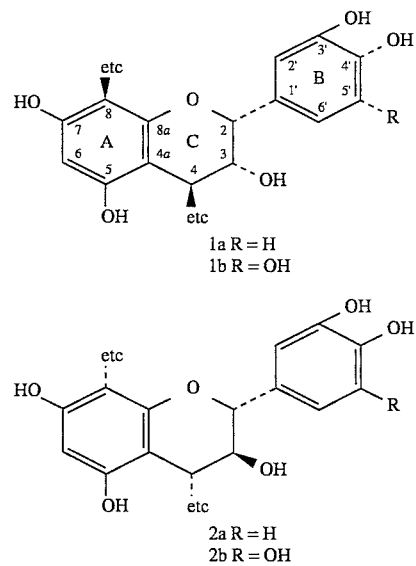

1a R = H
1b R = OH

2a R = H
2b R = OH

The monomer unit (generally termed "leucoanthocyanidin") of the polymer chain may be based on either of two stereochemistries of the C-ring, at the 2 and/or 4 position designated cis (called epicatechins) or trans (called catechin). Therefore, the polymer chains are based on different structural units, which create a wide variation of polymeric proanthocyanidins and a large number of possible isomers (Hemingway et al., 1982, *J.C.S. Perkin*, 1:1217). C13 NMR has been useful to identify the structures of polymeric proanthocyanidins and recent work has elucidated the chemistry of di-, tri- and and tetra-meric proanthocyanidins. Larger polymers of the flavonoid 3-ol units are predominant in most plants, and are found with average molecular weights above 2,000 daltons, containing 6 or more units, Newman et al., 1987, *Mag. Res. Chem.*, 25:118.

Proanthocyanidins have been reported to possess protein binding ability and a possible biological role (Newman et al., 1987, *Mag. Res. Chem.*, 25:118). Proanthocyanidin monomers and dimers have been used in the treatment of diseases associated with increased capillary fragility and have also been shown to have anti-inflammatory effects in experimental animals (Beladi et al., 1977, *Ann. N.Y. Acad. Sci.*, 284:358). A procyanidin monomer was found to have antiviral activity against Herpes Simplex virus in an in vitro assay. (Beladi, et al., supra.) Beladi et al. tested the viricidal effect of a number of flavonoid monomers including apigenin, pelargonidin, quercetin and a proanthocyanidin monomer on Herpes Simplex virus. The proanthocyanidin monomer was found to be the most effective in virus-inactivating activity, followed by pelargonidin and quercetin. Apigenin had only a slight effect. The effect of quercetin and the procyanidin monomer on the multiplication of Herpes Simplex virus in HEp-2 cells was also investigated. As concluded by Beladi et al., the monomeric flavonoids tested had viricidal activity, but only a slight inhibitory effect on virus multiplication in the in vitro assays.

Prior to the present invention, there has been no disclosure regarding the use of proanthocyanidins containing two or more flavonoid units for treating respiratory virus infections. Additionally, there has been no disclosure regarding the use of proanthocyanidins of six or more flavonoid units for treating virus infections in general.

For the purpose of the present application, a proanthocyanidin polymer isolated from the Croton species is designated "proanthocyanidin polymer A" and that isolated from *Calophyllum inophylum* is designated "proanthocyanidin polymer B". However, such designation is solely for simplicity of discussion and not necessarily intended to imply that the polymers are different classes of compounds. Both proanthocyanidin polymer A and proanthocyanidin polymer B are considered to be within the term proanthocyanidin polymer as described herein.

2.3 RESPIRATORY SYNCYTIAL VIRUS

Respiratory Syncytial Virus (RSV) belongs to the virus family Paramyxoviridae, genus Pneumovirus, and is responsible for causing lower respiratory tract infections such as bronchiolitis and pneumonia in the infant and child. The virus is considered to be in important agent of acute respiratory disease in children and it is expected that up to 50% of infants will suffer from RSV infections during their first winter. In young children with pulmonary or cardiac disease, up to a 37% mortality rate has been reported due to RSV. Although RSV respiratory infection is common in the young, the virus is found in respiratory secretions of infected persons of any age. Outbreaks among the elderly have been associated with serious and fatal illness, and RSV infection can be the source of fever and pulmonary infiltrates in immunosuppressed adults (Englund et al., 1988, *Ann. Int. Med.*, 1:203).

A vaccine of inactivated RSV has proven to be ineffective against RSV infection and leads to an unusual immune and lung inflammation upon subsequent RSV infection. Therefore, recent research has concentrated on developing either potent live vaccines or an effective antiviral compound.

Ribavirin, (1-β-D-ribofuranosyl-1, 2, 4-triazole 3-carboxamide), the current drug of choice, has been found to reduce the severity of illness and amount of virus shed in acute respiratory infections of RSV or influenza virus. Currently ribavirin is used for the treatment of RSV infections of the respiratory tract in aerosol form. However, because of its toxicity, ribavirin is less desirable for use systemically. Additionally, ribavirin has been found to be teratogenic in animals. This has raised serious concern for female health care personnel administering or exposed to ribavirin (Gladu et al., 1989, *J. Toxic Env. Health*, 28:1).

2.4 OTITIS MEDIA AND OTITIS EXTERNA

Otitis media, inflammation of the middle ear, is second only to colds as the most common disease of early childhood. More than 60% of all children will have an episode of otitis media by age six. The greatest risk for the development of acute otitis media lies in infections caused by respiratory syncytial viruses, rhinoviruses, influenza A viruses or adenoviruses (Henderson, et al., *N. Eng. J. Med.*, 1982, 1377; Ruuskanin, et al., *Pediatr. Infect. Dis. J.*, 1989, 94; Sanyai, et al., *J. Pediatr.*, 1980, 11). It has been found that prevention of the respiratory viral infection decreases the incidence of otitis media (Heikkinen, et al., *AJDC*, 445 (1991). Use of a flu vaccine has been found to be effective. However, there are a number of reasons why this is an unsatisfactory approach: it is necessary to administer the vaccine annually, two doses must be given initially, there is a problem of continual antigenic variation of the influenza viruses and the resulting fluctuation in efficacy of the vaccine and the cost.

2.5 INFLUENZA VIRUSES

Influenza viruses are members of the Orthomyxoviridae family and are distributed world-wide. Five pandemics have occurred in the 20th century, with the 1918 outbreak killing at least 21 million. In the United States, over 500,000 deaths have been attributed to influenza epidemics over the last twenty years. The outbreaks are seasonal, occurring almost every winter, and transmission is primarily through the respiratory route. Amantadine has been shown to shorten the fever duration and respiratory symptoms by only about 50%, but causes some central nervous system side effects. Rimantidine, as yet unlicensed, shows a similar effect, although it is not associated with the central nervous system side-effects seen with amantadine. Primary influenza viral pneumonia, a common complication of influenza infections, has not been shown to be treatable by either rimantidine or amantadine. Prophylactically, influenza has been controlled by the use of inactivated influenza virus vaccines with about 80% protective efficacy.

2.6 HERPES SIMPLEX VIRUS

Herpes simplex virus (HSV) is a member of the Herpitoviridae family, and is distributed world-wide. Transmission of the virus occurs via direct contact from person-to-person, with common entry of HSV-1 through the oral cavity and infection of HSV-2 through the genital tract. The prevalence of HSV antibody is inversely proportional to socioeconomic status, with close to 100% of HSV-positive adults in underdeveloped countries and 30–50% in developed countries. Acyclovir, idoxuridine (IDU or 2-deoxy-5-iodouridine), trifluridine and vidarabine (adenine arabinoside, Ara-A) are effective in treatment of various HSV infections, with trifluridine and acyclovir the drugs of choice. Vidarabine, the choice for ophthalmic infections, is not effective topically against herpes labialis or other skin/genital infections. Acyclovir is not effective topically when used against recurrent genital infections. However, it is effective when used i.v. and p.o. Acyclovir is not recommended for routine use in treatment of recurring HSV genital infections as ganglionic latency is still present and outbreaks occur after treatment is stopped.

3. SUMMARY OF THE INVENTION

The present invention relates to a method of treating respiratory virus infections, comprising administering to a warm-blooded animal, a therapeutically effective amount of an antiviral agent comprising a proanthocyanidin polymer. The proanthocyanidin polymer preferably contains 2 to 30 flavonoid units, more preferably 2 to 15 flavonoid units, and most preferably 2 to 11 flavonoid units. The flavonoid units include but are not limited to catechins, epicatechins, gallocatechins, galloepicatechins, flavanols, flavonols, flavandiols, leucocyanidins, anthocyanidins, or combinations thereof. The flavonoid units can be singly or doubly linked to each other. More specifically, the method of the invention can be used to treat respiratory infections induced by a respiratory syncytial virus as well as Parainfluenza virus 3, Influenza A, Influenza B virus and virus associated with otitis media and otitis externa. The proanthocyanidin polymer can be administered intravenously, intraperitoneally, subcutaneously, intramuscularly, orally, topically, or by inhalation.

The proanthocyanidin polymers are effective against most of the viruses implicated in otitis media. They are soluble in aqueous solutions, are readily formulated for parenteral, oral, topical (i.e., into ear and nose) administration and thus are admirably suited for use in the prophylaxis or treatment of otitis media.

The proanthocyanidin polymers are similarly effective against the viruses implicated in otitis externa. Because such viruses are located outside of the tympanic membrane, the proanthocyanidin polymers can be topically administered into the ear in a suitable formulation so as to come directly into contact with the viruses.

The proanthocyanidins useful for treating respiratory virus infections have a structure selected from I, II, and III, and their esters, or ethers or the corresponding oxonium salts

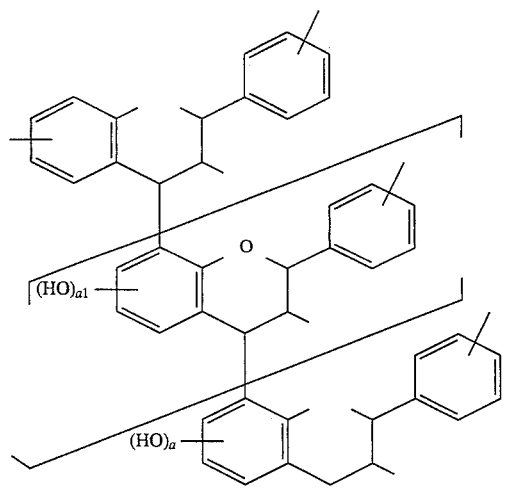

I

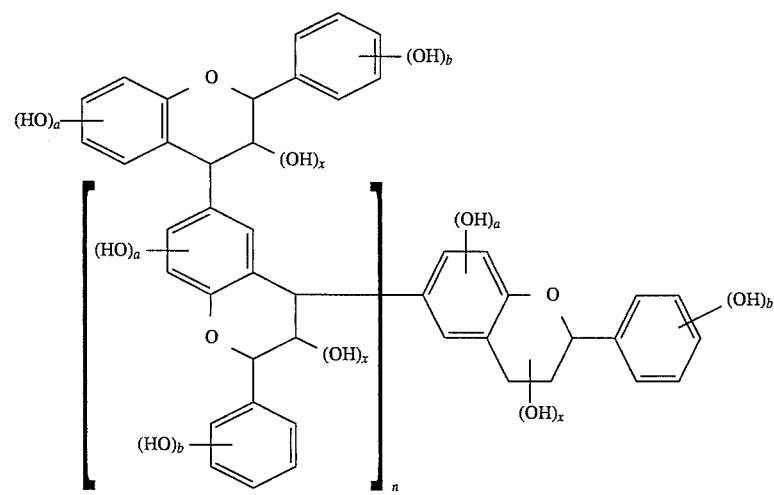

II

-continued

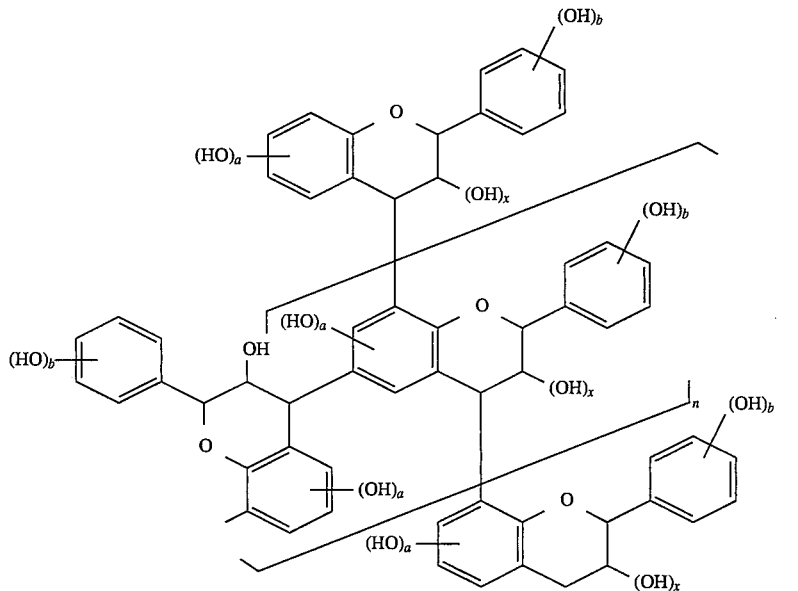

III where a, b=1 to 3, x=0 or 1, n=0 to 28, preferably 0 to 13, more preferably 0 to 9.

The proanthocyanidin polymer useful for treating a respiratory virus infection can comprise 2 to 30, preferably 2 to 15, most preferably 2 to 11 monomeric flavanoid units having structure IV, or esters, ethers or corresponding oxonium salts thereof.

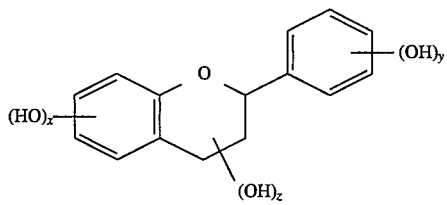

IV where x, y=1 to 3, z=1 or 2.

Another embodiment of the invention further relates to a method of treating virus infections comprising administering, to a warm-blooded animal, a therapeutically effective amount of antiviral agent comprising a proanthocyanidin polymer containing 6 to 30 flavonoid units, preferably 6 to 15 flavonoid units and more preferably 6 to 11 flavonoid units. The flavonoid units include but are not limited to catechins, epicatechins, gallocatechins, galloepicatechins, flavanols, flavonols, flavandiols, leucocyanidins, anthocyanidins, or combinations thereof. The flavonoid units can be singly or double linked to each other. The method can be used to treat virus infections which are caused by paramyxovaridae, orthomyxovaridae or herpes viruses. The proanthocyanidin polymer can be administered intravenously, intraperitoneally, subcutaneously, intramuscularly, orally, topically, or by inhalation.

The present invention also relates to proanthocyanidins useful for treating virus infections in general having a structure selected from I, II, and III, above, and esters, ethers and corresponding oxonium salts thereof, where n=4 to 28, preferably 4 to 13, most preferably 4 to 9.

The present invention also relates to novel proanthocyanidins which are obtained from a Croton species and from a *Calyphyllum inophylum* species and their esters, ether and oxonium derivatives. Such proanthocyanidin can be isolated from the whole plant, the bark, the leaves, the roots or the latex. In a preferred embodiment, the proanthocyanidin can be obtained from *Croton lechleri* and from *Calophyllum inophylum*. These novel proanthocyanidin polymers are characterized by IR, UV-visible, and/or $^{13}C$ NMR spectroscopy.

4. BRIEF DESCRIPTION OF THE FIGURES

FIG. 1 Fourier-transform infra-red spectrum of proanthocyanidin polymer A isolated from the Croton tree.

Figure 2:
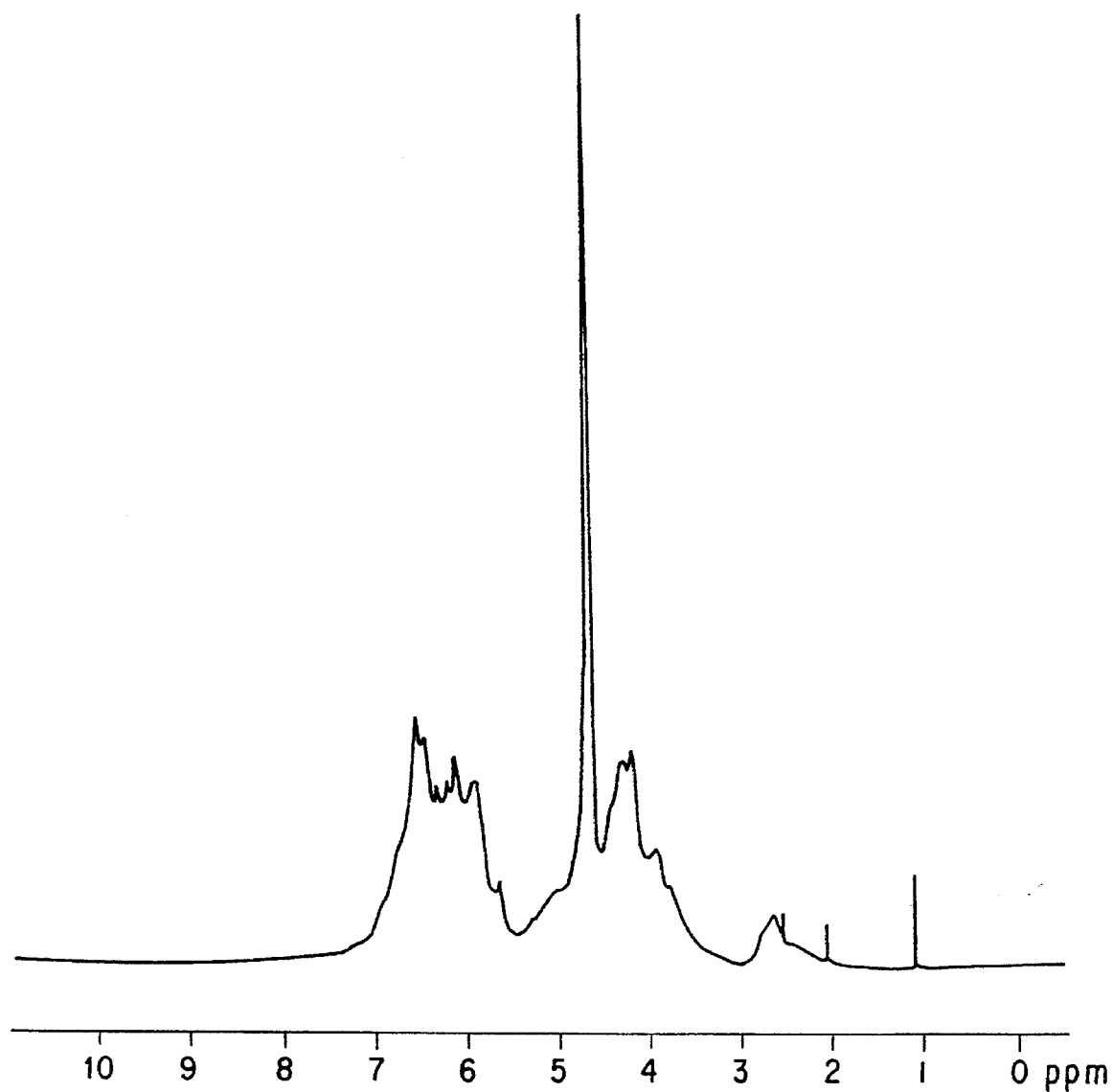

FIG. 2 $^1H$ Nuclear magnetic resonance spectrum of proanthocyanidin polymer A isolated from the Croton tree. Sample was in $D_2O$ at 400 MHz.

Figure 3:
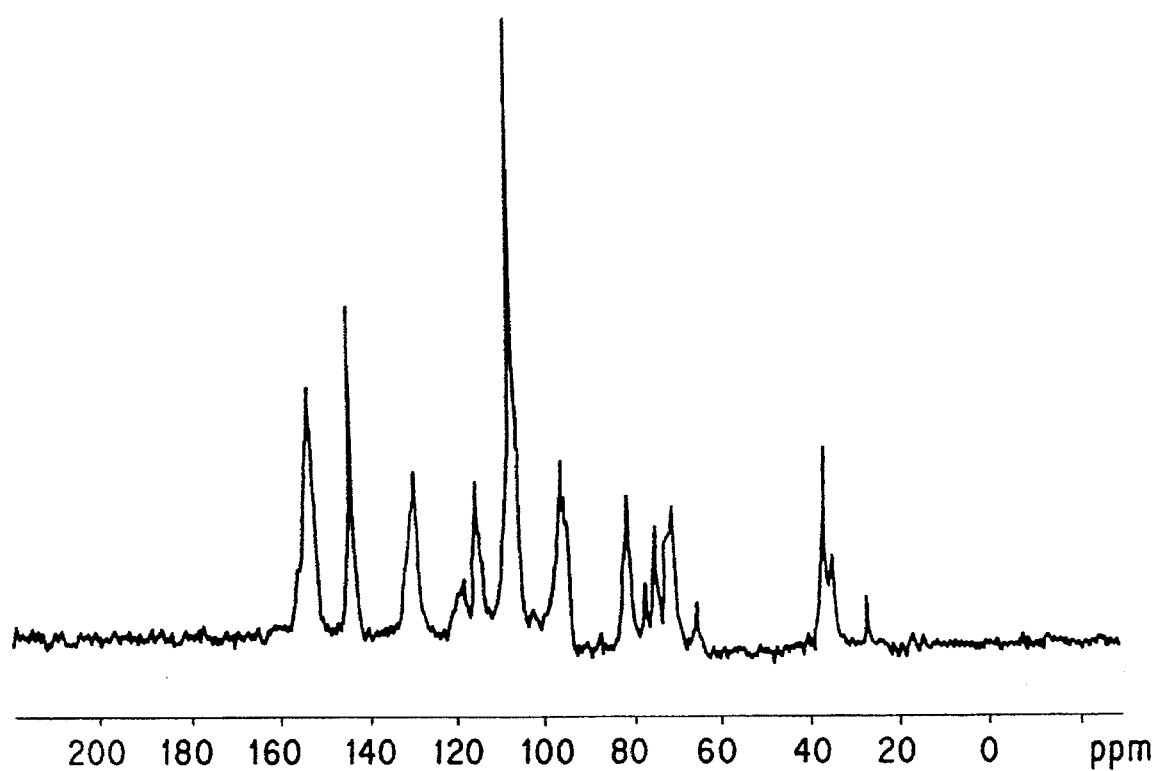

FIG. 3 Broad-band decoupled $^{13}C$ nuclear magnetic resonance spectrum of proanthocyanidin polymer A in $D_2O$ at 100 MHz.

Figure 4:
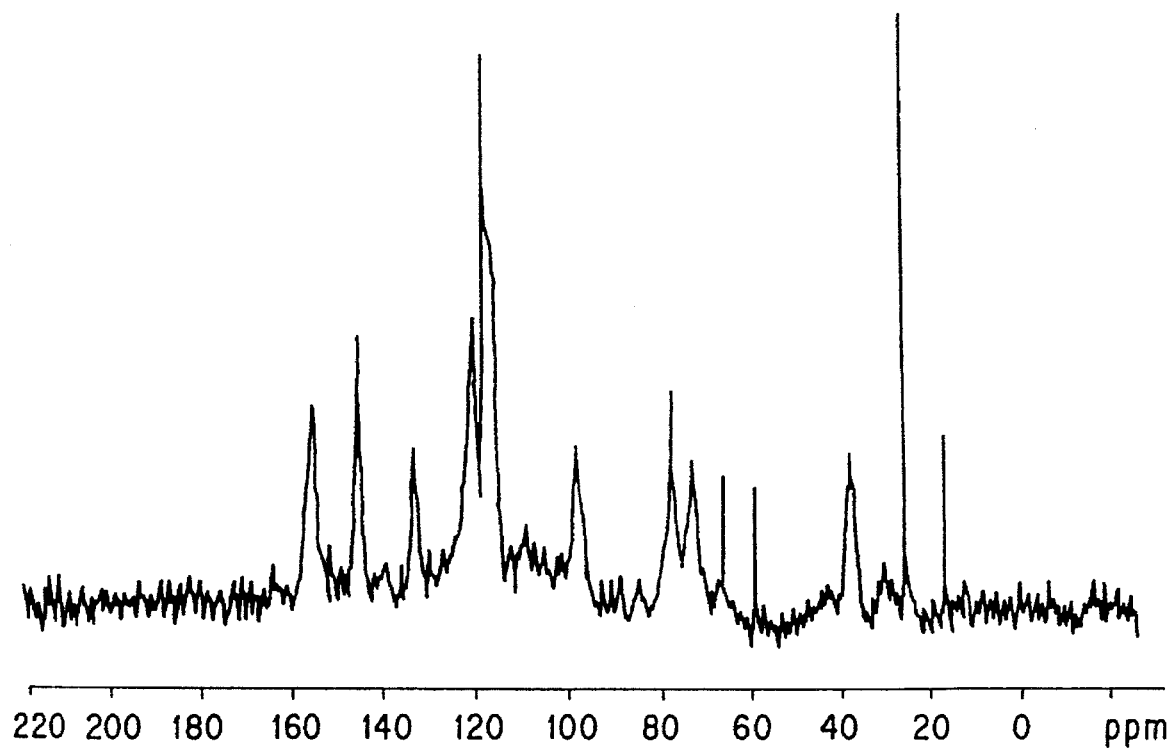

FIG. 4 The $^{13}C$ NMR spectra of proanthocyanidin polymer B isolated from *Calophyllum inophylum*, obtained at 100 MHz in $D_2O$.

Figure 5:
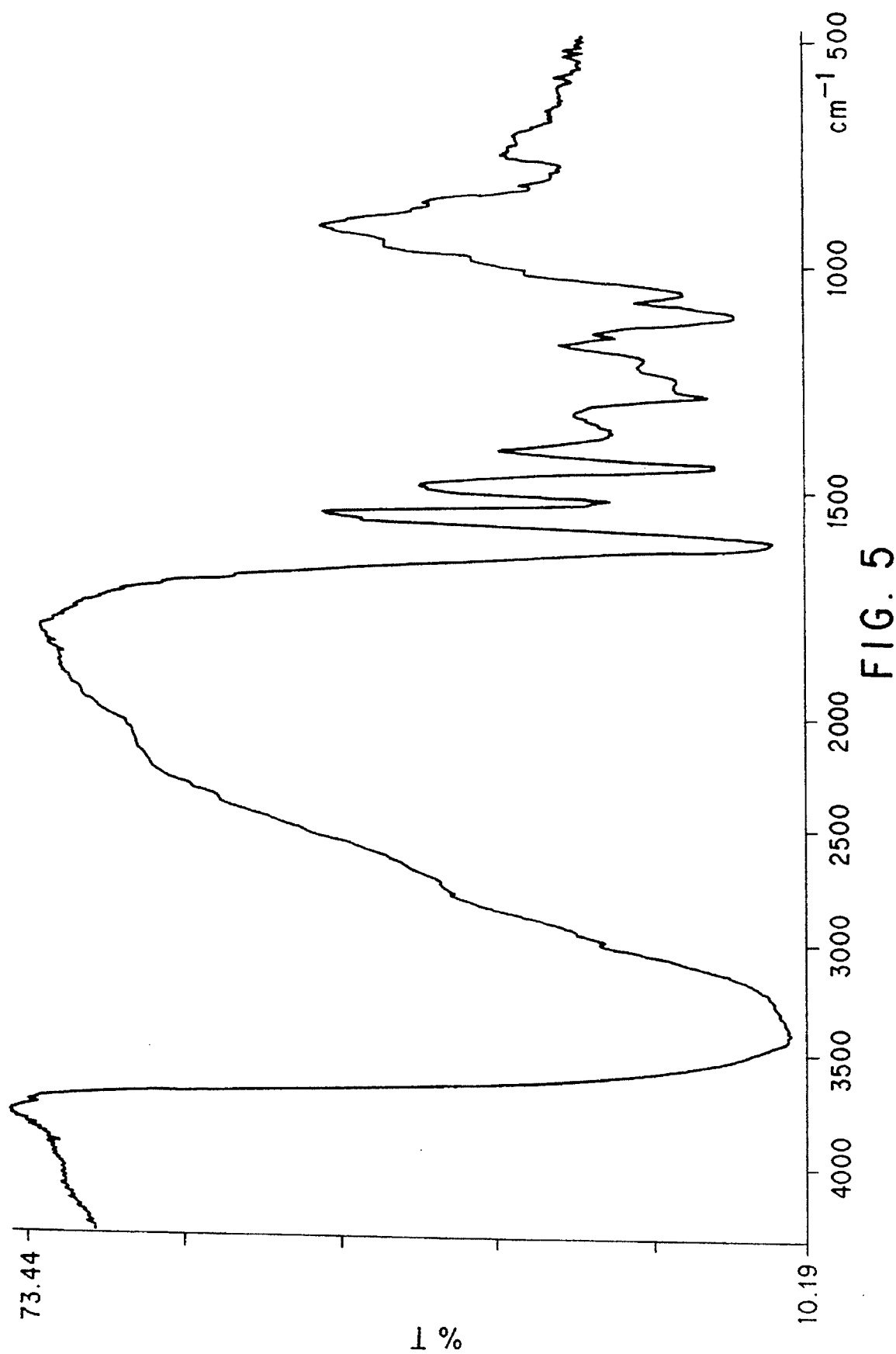

FIG. 5 Fourier-transform infra-red spectrum of proanthocyanidin polymer B isolated from *Calophyllum inoplylum*.

Figure 6:
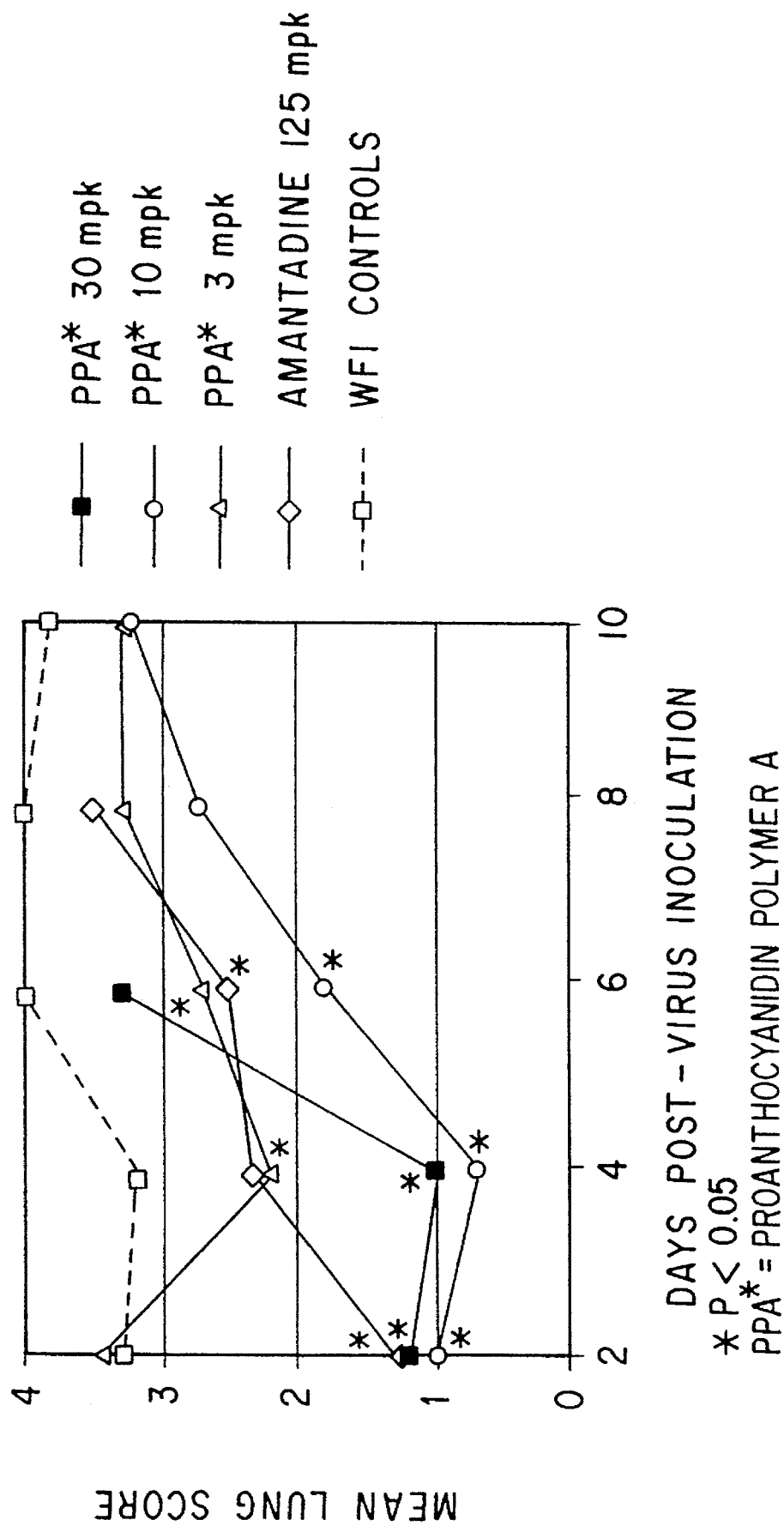

FIG. 6 The effect of proanthocyanidin polymer A and Amantadine on lung consolidation in mice infected with influenza A (HlN1) virus (early treatment initiation).

Figure 7:
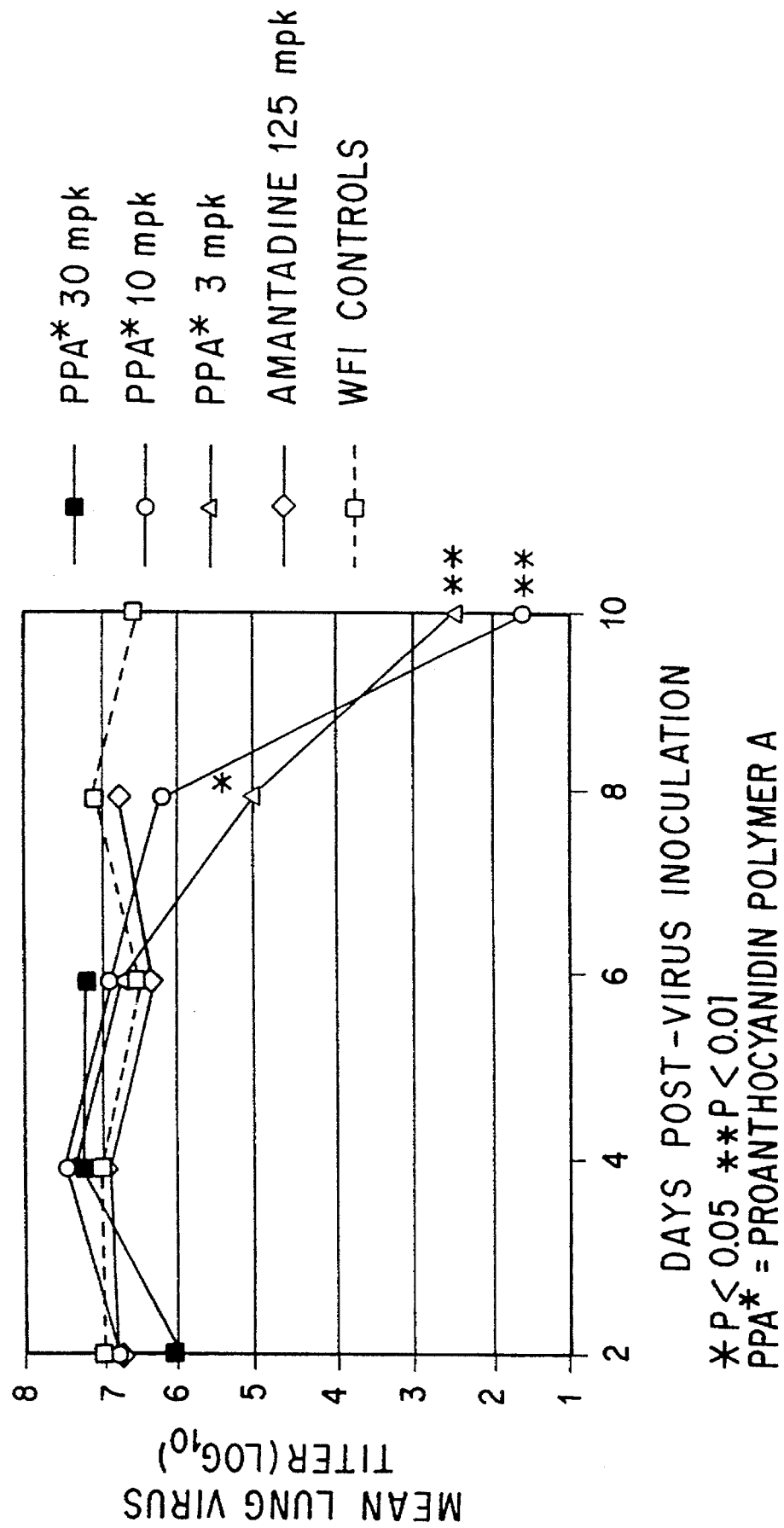

FIG. 7 The effect of proanthocyanidin polymer A and Amantadine on lung virus titers in mice infected with influenza A (HlN1) virus (early treatment initiation).

Figure 8:
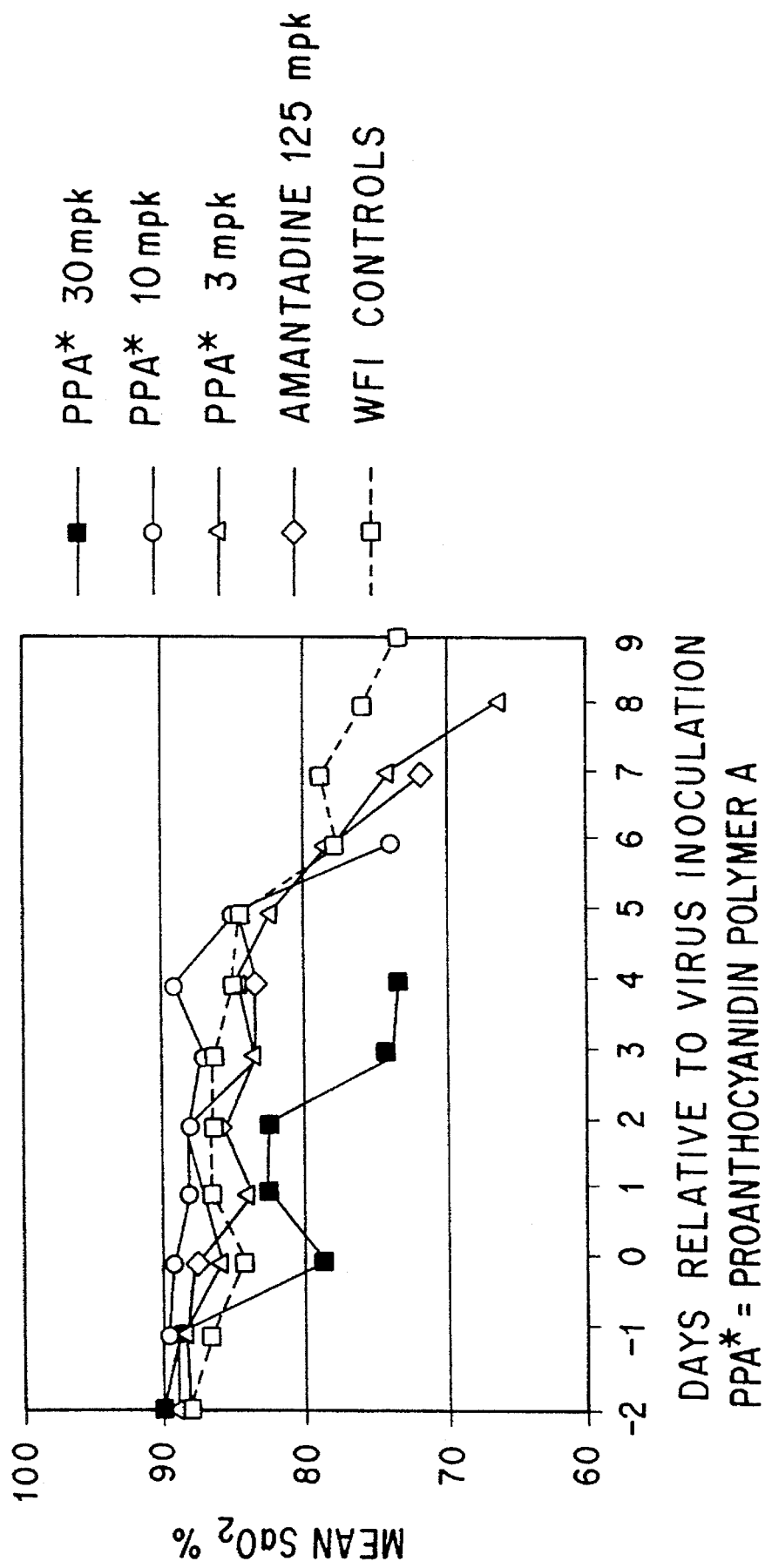

FIG. 8 The effect of proanthocyanidin polymer A and Amantadine on arterial oxygen saturation ($SaO_2$) in male mice infected with influenza A (HlN1) virus (early initiation).

Figure 9:
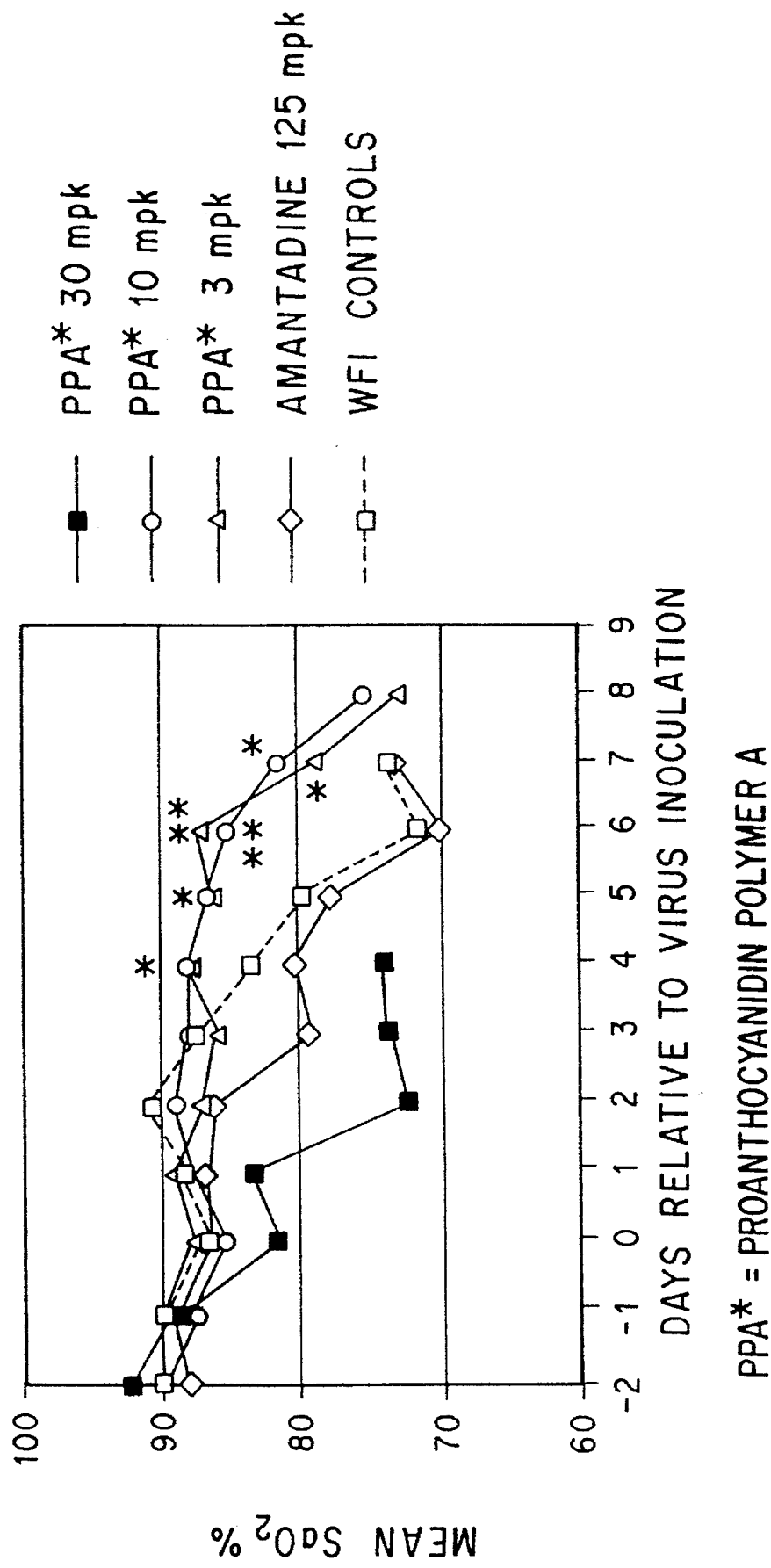

FIG. 9 The effect of proanthocyanidin polymer A and Amantadine on arterial oxygen saturation ($SaO_2$) in female mice infected with influenza A (HlN1) virus (early treatment initiation).

Figure 10:
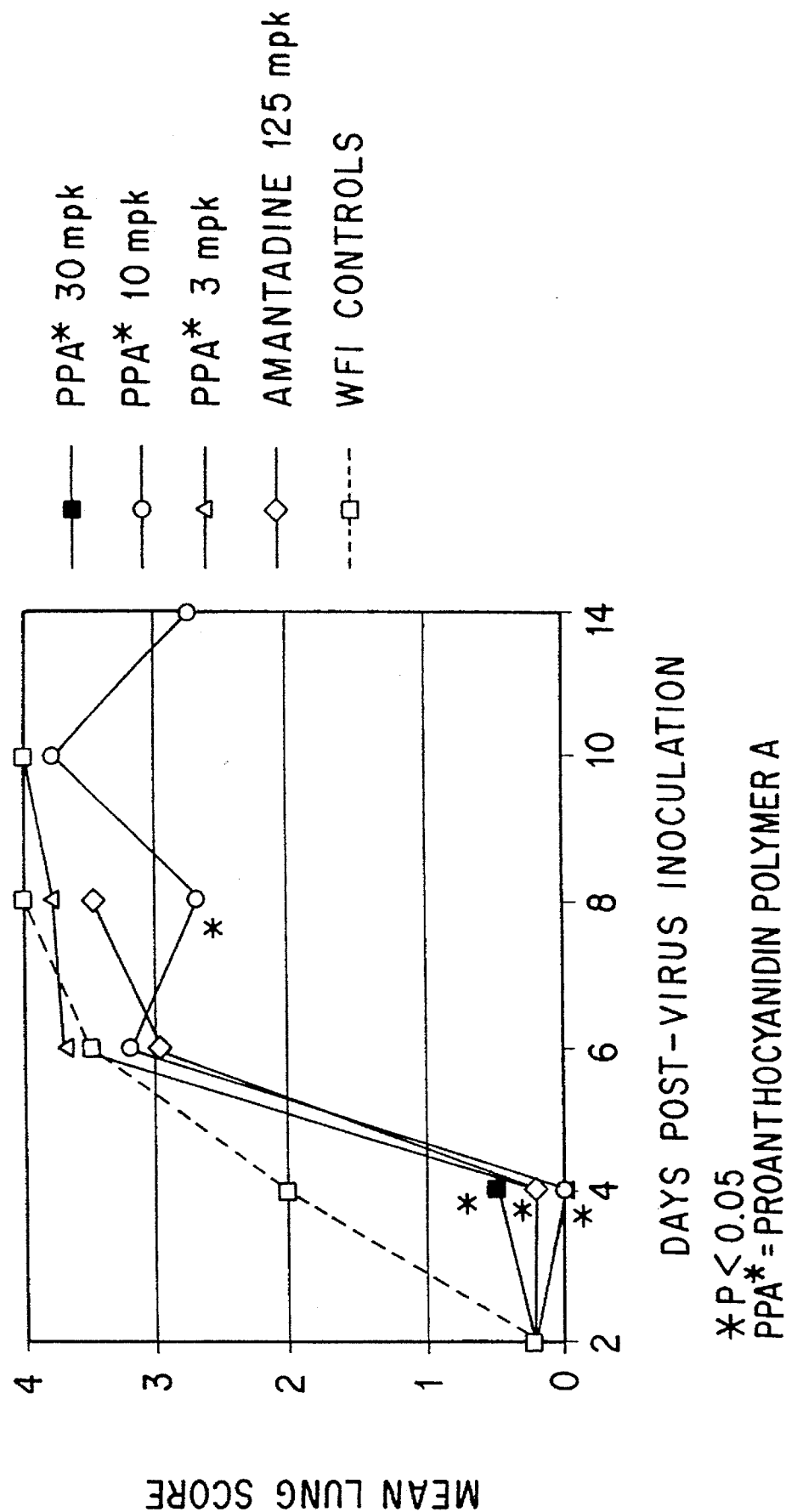

FIG. 10 The effect of proanthocyanidin polymer A and Amantadine on lung consolidation in mice infected with influenza A (HlN1) virus (late treatment initiation).

Figure 11:
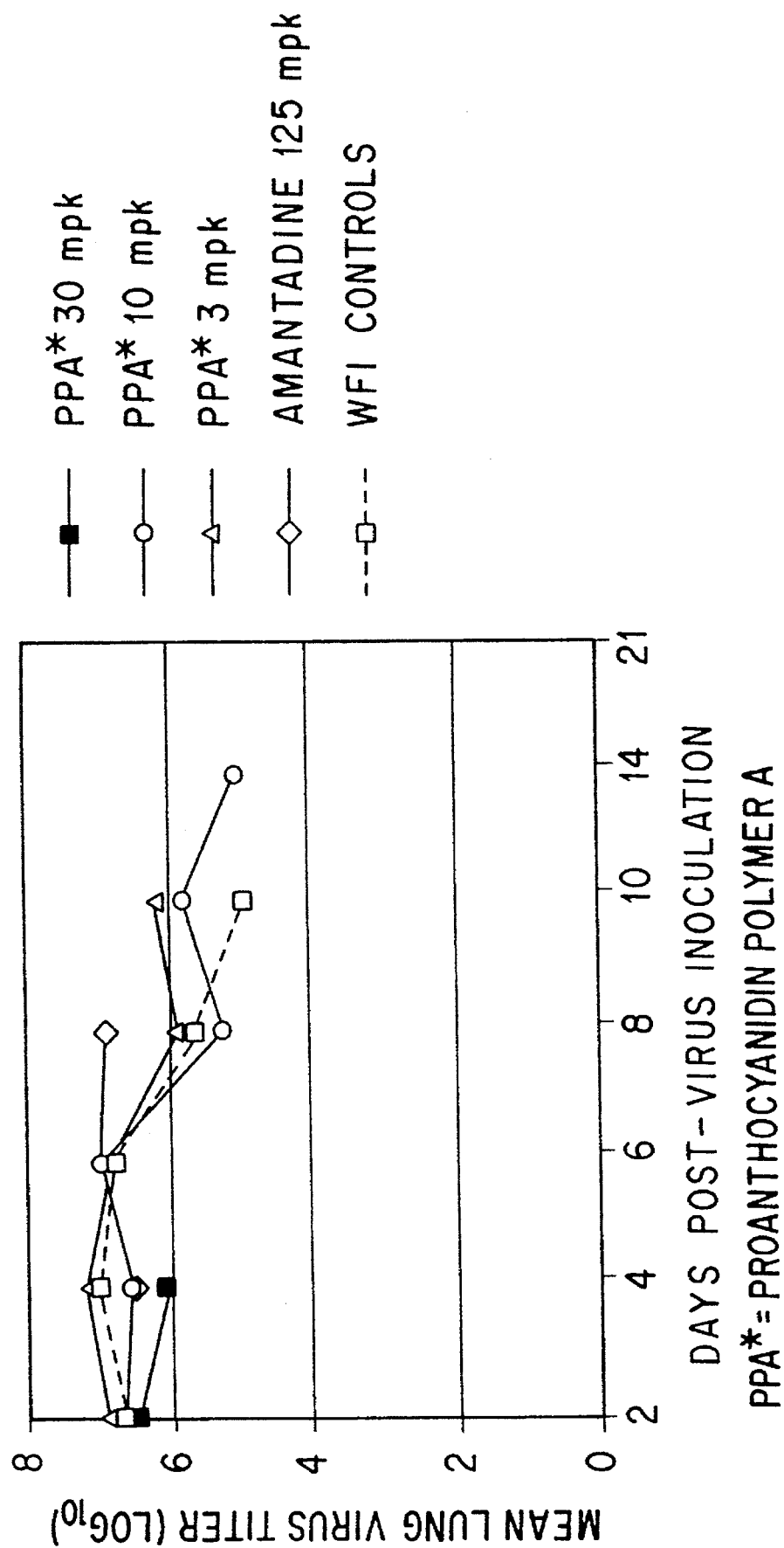

FIG. 11 The effect of proanthocyanidin polymer A on lung titers in mice infected with influenza A (HlN1) virus (late treatment initiation).

Figure 12:
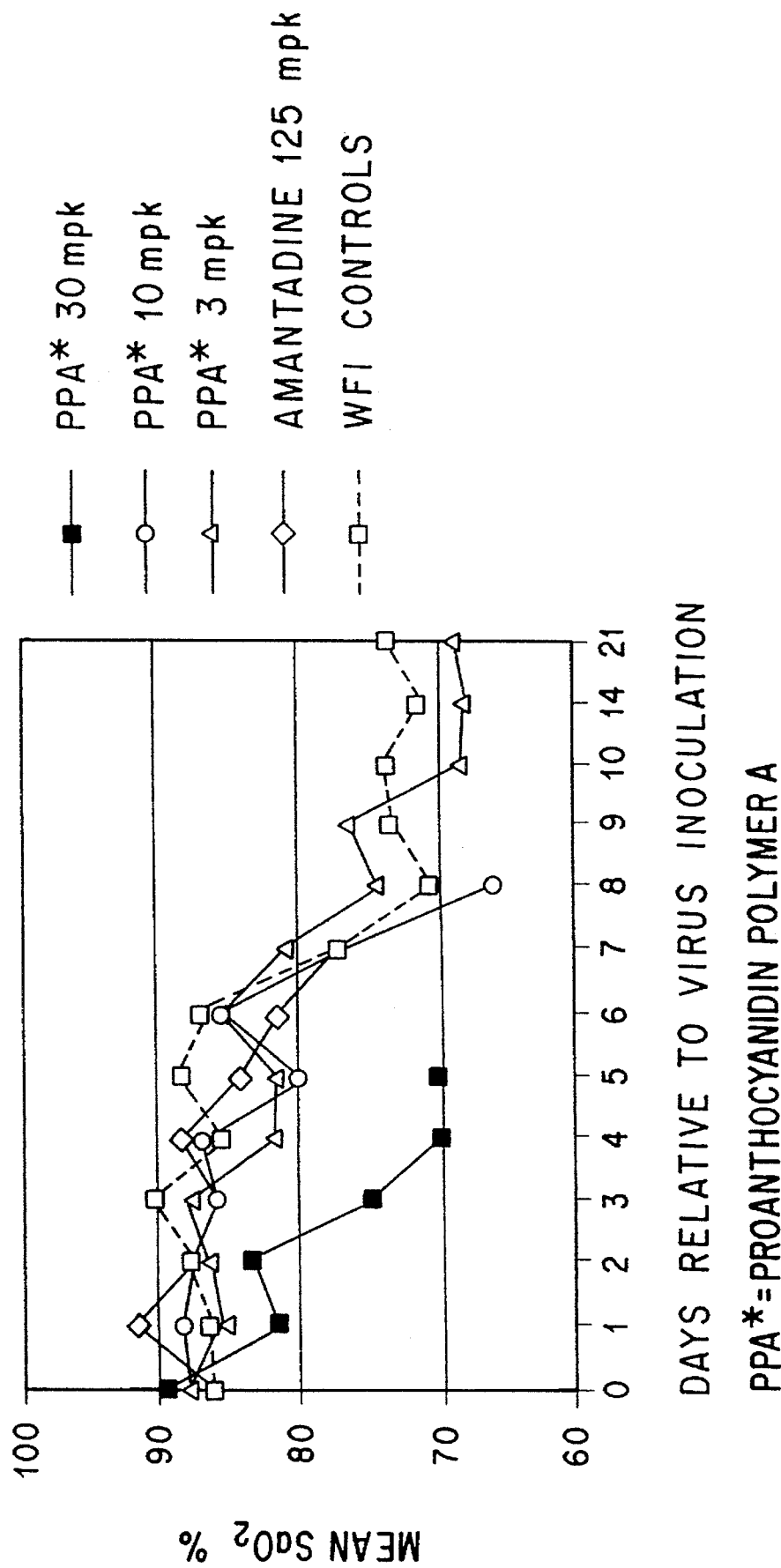

FIG. 12 The effect of proanthocyanidin polymer A and Amantadine on arterial oxygen saturation ($SaO_2$) in male mice infected with influenza A (HIN1) virus (late treatment initiation).

Figure 13:
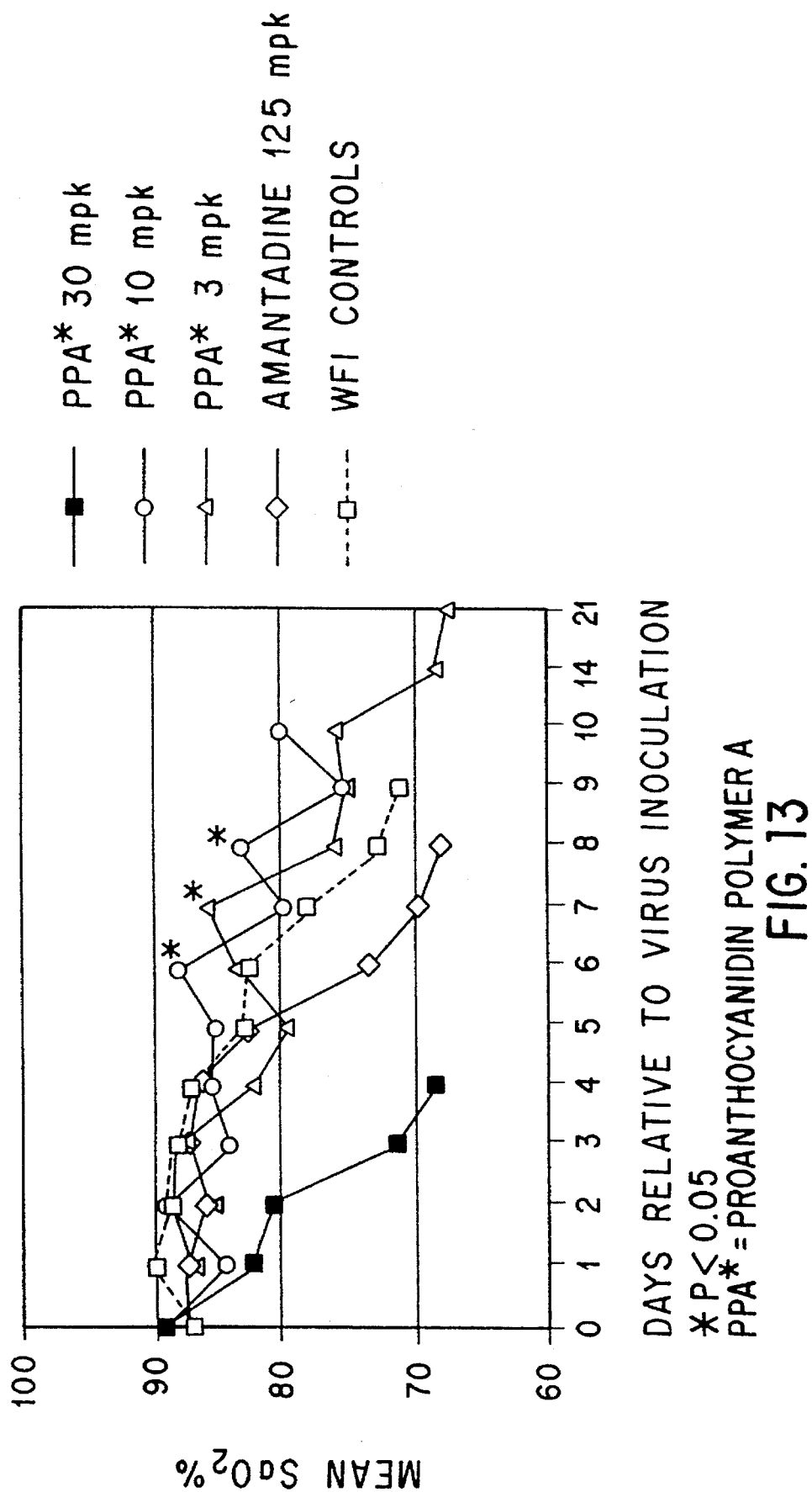

FIG. 13 The effect of proanthocyanidin polymer A and Amantadine on arterial oxygen saturation ($SaO_2$) in female mice infected with influenza A (HIN1) virus (late treatment initiation).

Figure 14:
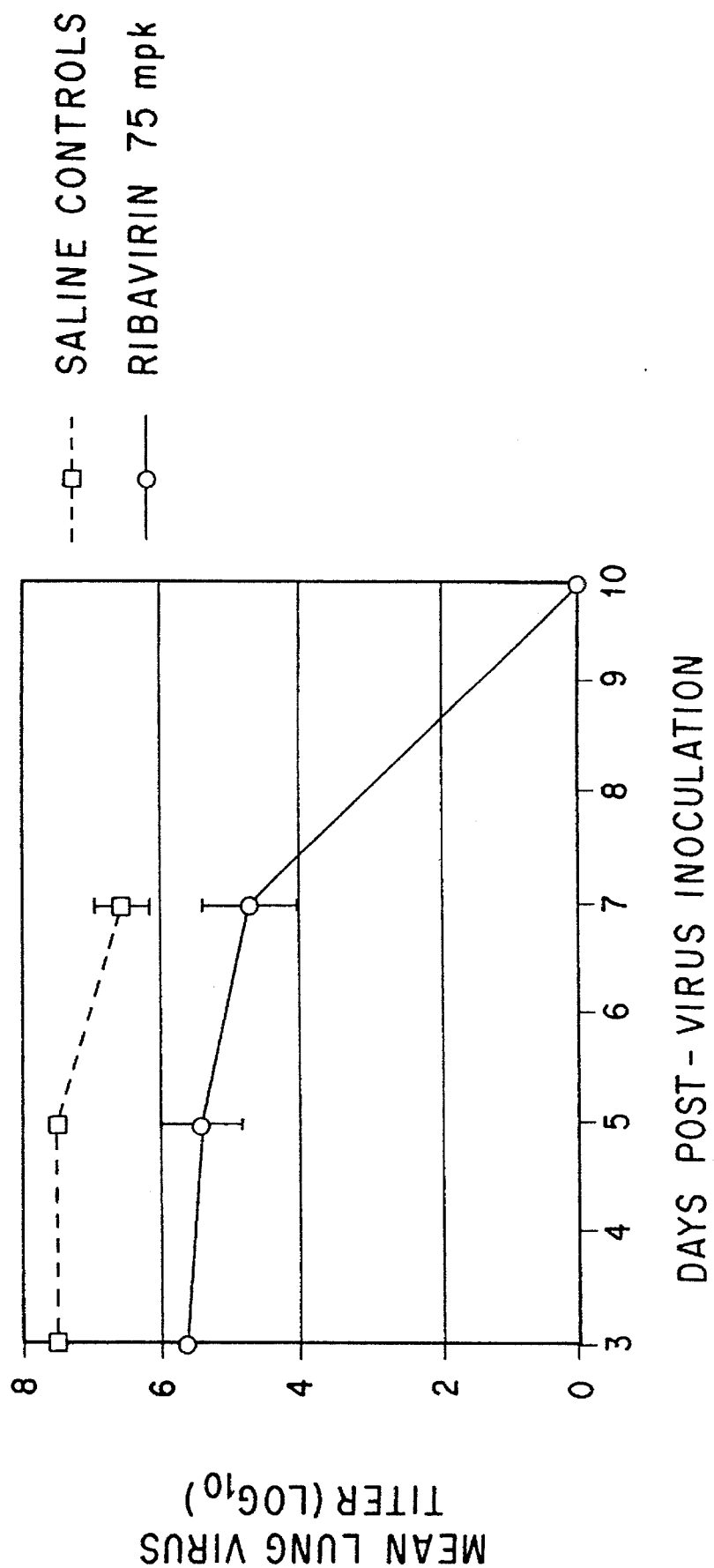

FIG. 14 The effect of Ribavirin on lung virus titers in mice infected with influenza A (HIN1) virus.

Figure 15:
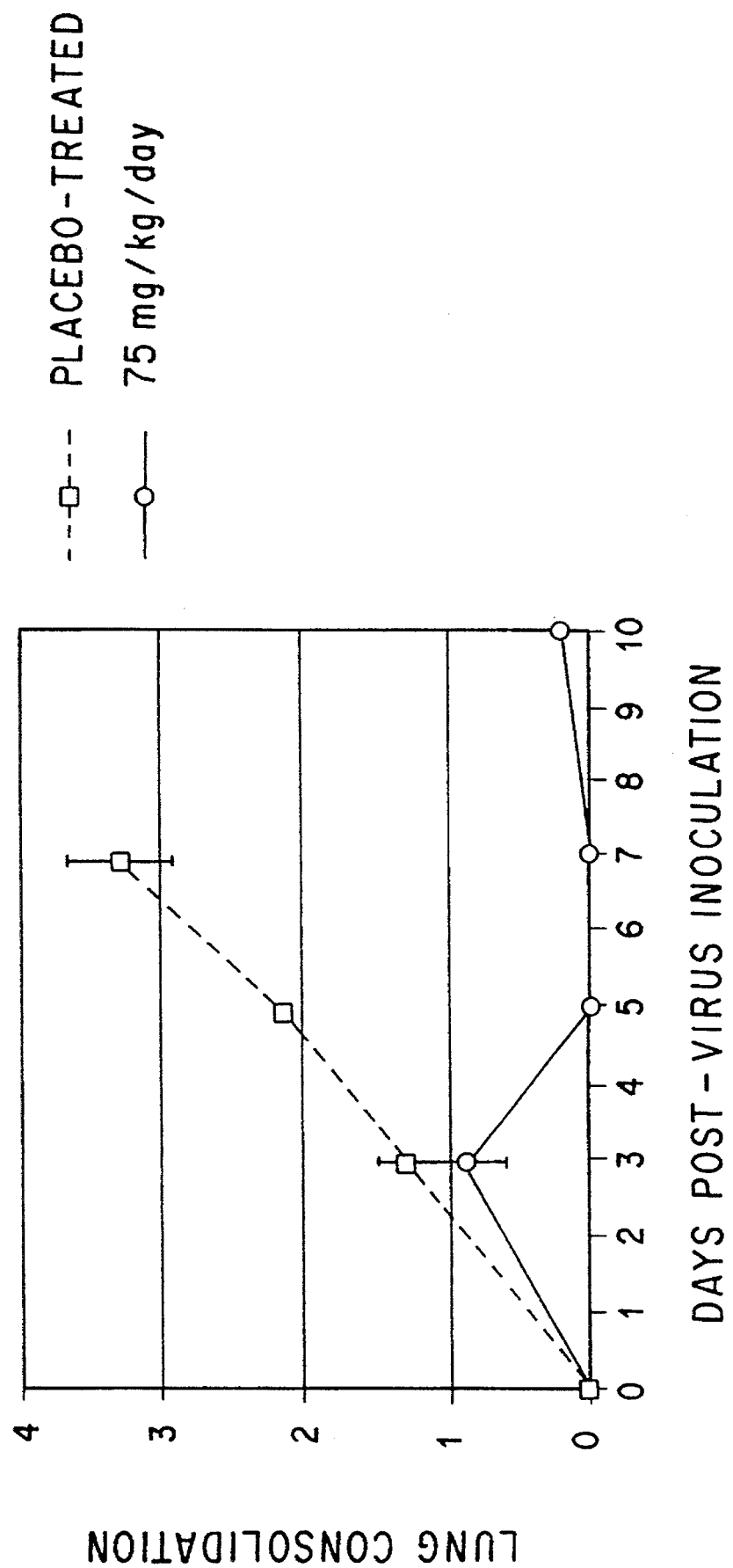

FIG. 15 The effect of intraperitoneal Ribavirin treatment on lung consolidation in influenza A (HIN1) virus infected mice.

Figure 16:
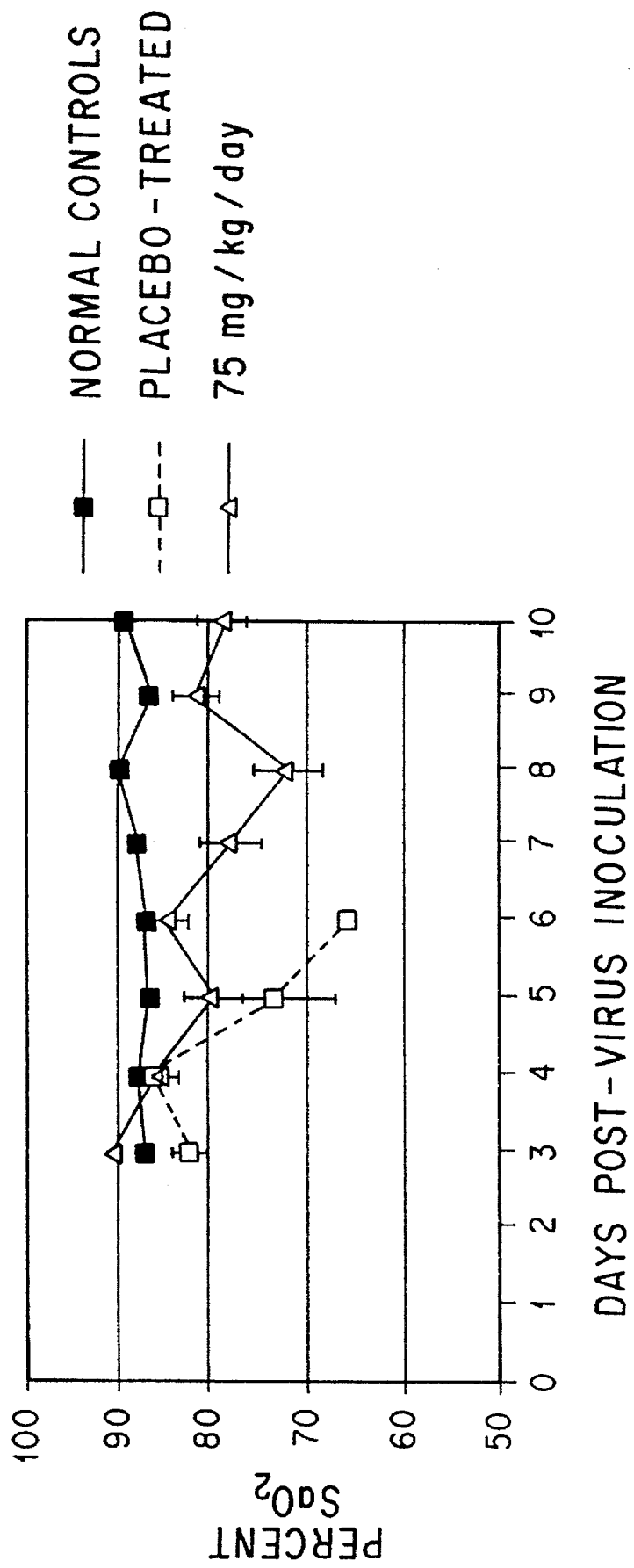

FIG. 16 The effect of intraperitoneal Ribavirin treatment on blood $SaO_2$% in influenza A (HIN1) virus infected mice.

FIG. 17 The effect of proanthocyanidin polymer A and Ganciclovir on HSV-2 vaginal lesions in mice.

FIG. 18 The effect of proanthocyanidin polymer A in 5% and 10% typical formulations, compared to placebo and acyclovir, in a 5% topical formulation.

5. DETAILED DESCRIPTION OF THE INVENTION

5.1 USEFUL PROANTHOCYANIDIN POLYMERS

Proanthocyanidin oligomers or polymers, useful for the present anti-viral method are comprised of monomeric units of leucoanthocyanidins. Leucoanthocyanidins are generally monomeric flavonoids which include catechins, epicatechins, gallocatechins, galloepicatechins, flavanols, flavonols, and flavan-3,4-diols, leucocyanidins and anthocyanidins. The proanthocyanidin polymers useful for treating respiratory virus infections have 2 to 30 flavonoid units, preferably 2 to 15 flavonoid units, and most preferably 2 to 11 flavonoid units. The proanthocyanidin polymers useful for treating virus infections in general, including but not limited to, infections related to influenza viruses, parainfluenza viruses, viruses of the types known as paramyxoviridae, orthomyxovaridae, and herpes viruses, have 6 to 30 flavonoid units, preferably 2 to 15 flavonoid units, and most preferably 6 to 11 flavonoid units.

Proanthocyanidin polymers having a varying number of flavonoid units are known and have been reported, for example, in W. L. Mattice, et al. Phytochemistry, 23, p. 1309–1311 (1984); Z. Czochanska, et al. J.C.S. Chem. Comm., 375 (1979); W. T. Jones, et al. Photochemstry, 15, p. 1407–1409 (1976); E. Haslam *Plant Polyphenols*, p. 75 (1989), which are all incorporated by reference. Those polymers havings the recited ranges of flavonoids units and described in these references are useful for the methods of the present invention.

5.2 METHODS FOR OBTAINING USEFUL PROANTHOCYANIDIN POLYMERS

5.2.1 ISOLATION

Useful proanthocyanidin polymers are obtained from various plants including but not limited to the classes Filices, Coniferae, Monocotyledoneae, and Dicotyledonae (J. B. Harborne, THE FLAVONOIDS, ADVANCES IN RESEARCH SINCE 1980 (1988)). They can be obtained using the entire tree or plant, the bark, stems, roots or latex.

These plant source materials are extracted with water and/or a water miscible solvent. The preferred solvents are alcohol of 1–3 carbon atoms or acetone. The aqueous extract is used directly or after solvent removal. If the solvent is removed, the solid residue is redissolved in a solvent, preferably a lower alcohol or acetone, and insoluble materials are discarded. The soluble fraction is subjected to gel filtration (e.g., over a Sephadex), reversed-phase column chromatography (e.g., C-8), or gel-permeation chromatography (e.g., divinyl benzene cross-linked gels) such as PL-GEL or membranes (e.g., an Amicon membrane) using water or water and a water miscible solvent, with or without a buffer, as the mobile phase. The water miscible solvent is preferably a 1–3 carbon alcohol, acetone or acetonitrile.

The useful proanthocyanidin polymers of this invention are the fractions detected by ultraviolet (uv). They have their major UV absorption maxima between about 200–350 nm, with peaks usually at 200–210 nm, and 275–285 nm.

With regard to the novel proanthocyanidin polymer compositions which form part of the basis of this invention, such polymers can be obtained from the Croton tree or Calophyllum species by using the above-described extraction method. The soluble fraction is subjected to gel filtration, reversed-phase column chromatography, gel-permeation chromatography, or membranes. Using water or water and a water miscible solvent, with or without a buffer as the mobile phase and the relevant fractions containing the polymers are detected using uv at a range of about 200–350 nm.

According to a preferred embodiment of the present invention, a novel proanthocyanidin polymer can be prepared as follows: Latex obtained from a Croton tree (e.g., *Croton lechleri*) or from *Calophyllum inophylum* is used directly or is concentrated by the removal of water (e.g., lyophilized). It is extracted with water, a lower alcohol of about 1–3 carbons, or with acetone to give an aqueous soluble fraction. The aqueous-soluble fraction of the lyophilized or otherwise concentrated material is subjected to partitioning by ethyl acetate/water solution and to gel filtration (e.g., Sephadex) using water and/or water and alcohol and/or water and acetone, with or without a buffer as the mobile phase. The fractions containing a chromophoric band are detected by ultraviolet (uv) (λmax about 200–350 nm) and collected and concentrated and subjected to gel filtration again, if necessary, to yield the proanthocyanidin polymer. Alternatively, the aqueous-soluble fraction described above is lyophilized or concentrated or is used directly and is subjected to reversed-phase column chromatography (RP HPLC), using water and/or water and acetone and/or water and alcohol as the mobile phase. The fractions containing a chromophoric band detected by uv (max about 200–350 nm) are collected and concentrated, and subjected to RP HPLC again, if necessary, to yield the proanthocyanidin polymer. Alternatively, the aqueous-soluble fraction, described above, is lyophilized, concentrated or is directly subjected to gel permeation chromatography (GPC), using water and/or water and alcohol and/or water and acetonitrile, with or without a buffer, as the mobile phase. The fractions containing a chromophoric band detected by uv at λmax about 195–350 nm are collected and concentrated and subjected to GPC again, if necessary, to yield the proanthocyanidin polymer. See examples in Sections 6.1–6.3, infra.

As demonstrated in Section 6.2 when chromatographed on a Perkin Elmer LC-620 using Polymer Labs PL-gel 5 m 500 A, 300×7.5 mm and THF-water (95:5 v/v) system at a flow rate of 1 ml/min, proanthocyanidin A has a retention time of 7.2 min. and proanthocyanidin B has a retention time of 6.5 min. Typical spectra for proanthocyanidin polymers are shown in FIGS. 1 and 5.

5.2.2 SYNTHESIS OF USEFUL PROANTHOCYANIDIN POLYMERS AND DERIVATIVES THEREOF

It is known that leucoanthocyanidins can be condensed in mildly alkaline or acidic solutions to form proanthocyanidins. As an example, L. Y. Foo and R. W. Hemingway, *J. Chem. Soc., Chem. Commun.*, 85 (1984) were able to synthesize a trimer from flavanol monomers. J. A. Delcoun, et al., *J. Chem. Soc. Perkin Trans. I.*, 1711 (1983) teaches that under mild, low pH, conditions and an excess amount of (+)-catechin, condensation occurred to form higher and predominantly linear [4,8]-linked oligomers. Specifically, dimers, trimers and tetramers of the flavonoid analogues were synthesized and characterized by NMR spectroscopy. By use of such condensation reactions proanthocyanidin polymers of up to about 30 flavonoid units can be synthesized for use in the methods of the invention. As an alternative to the above synthesis, enzymatic synthesis can be employed to produce the useful proanthocyanidin polymers. The novel proanthocyanidin polymer compositions of the present invention specifically exemplified herein can also be synthesized by such reactions.

Esters of proanthocyanidin polymers can be prepared by standard methods of acylation such as by the reaction of the polymer with acid chlorides or acid anhydrides in the presence of base. Of particular utility is the preparation by reaction with acid anhydrides in pyridine as utilized for the acylation of certain other lower molecular weight flavonoids by Thompson, et al., *JCS*, 1387 (1972), Fletcher, et al., *JCS*, 1628 (1977) and Hemingway, *JCS*, 1299 (1982).

Ethers can be prepared by standard methods of etherification such as by reaction of the polymer with alkyl halides and alkyl tosylates in bases. Methyl ethers are readily prepared by the use of diazomethane as utilized in the etherification of certain other low molecular weight flavonoids by Thompson, JCS, 1387 (1972), Hemingway, *JCS*, 1299 (1982).

The oxonium salts (sometimes referred to as pyrilium salts or anthocyanidins) may be prepared by the so-called Bate-Smith reaction (*Chemistry and Industry*, 1953, 377), by warming with aqueous or alcoholic acids (see also, Thompson, et al., *JCS*, 1387 (1972) and references cited in Haslam, PLANT POLYPHENOLS, 1989, p. 28, Cambridge Press). This reaction can be advantageously catalyzed by iron (Porter et al., *Phytochemistry*, 25, 223 (1986)).

5.3 CHARACTERIZATION OF NOVEL PROANTHOCYANIDIN POLYMERS

Novel proanthocyanidin polymers prepared according to the present invention have solubility in methanol and water. The polymers are soluble in water and aqueous solution including alcohol solutions to a degree of at least about 10 mg/ml.

The proanthocyanidin polymers have been analyzed by a number of methods to determine their molecular weight and various other chemical and physical features. Various stereoisomers of proanthocyanidin polymers have been obtained and are within the scope of the present invention.

Column chromatography has been used to isolate water soluble fractions containing novel proanthocyanidin polymers varying in average molecular weight from about 700 daltons to about 3000 daltons, which corresponds to 2–3 to 9–11 average flavonoid units, respectively.

$^{13}$C-NMR spectroscopy indicates that the proanthocyanidin polymers contain flavonoid moieties in which the individual flavonoid ring units possess various stereochemistries.

UV-visible spectroscopy is consistent with the possible presence of a flavylium moiety or moieties within certain of the proanthocyanidin polymers.

The characterization of proanthocyanidin polymer A and proanthocyanidin polymer B is further discussed in the examples at Sections 6.3 and 6.5. Functional derivatives of these polymers can be made and may be useful as intermediate for the preparation of useful proanthocyanidin polymers.

5.4 PROPHYLACTIC AND THERAPEUTIC USES OF PROANTHOCYANIDIN POLYMERS

Proanthocyanidin polymers have been shown to be active in vitro and in vivo against a wide variety of viruses, and can be advantageously used in prophylactic and therapeutic applications against diseases induced by such viruses.

The proanthocyanidin polymers can be used either alone or in combination with other antiviral or antimicrobial agents to prevent and/or treat diseases induced by or complicated with viral infections from viruses including, but not limited to: paramyxovaridae such as respiratory syncytial virus, orthomyxovaridae such as influenza A, B and C, and herpes viruses such as Herpes Simplex virus.

Proanthocyanidin polymers have various advantages in the treatment of viral infections including, but not limited to:

1) a broad range of antiviral activity;
2) very low toxicity;
3) no teratogenicity; and
4) application to both systemic as well as localized (i.e., topical) applications.

5.5 ROUTES OF ADMINISTRATION

The proanthocyanidin polymers of the present invention can be administered for prophylactic and therapeutic applications by a number of routes, including but not limited to: oral, injection including but not limited to, intravenous, intraperitoneal, subcutaneous, intramuscular, etc., by topical application such as to nasal, nasopharyngeal linings and into the ear, and by inhalation via aerosolization and application to respiratory tract linings, etc.

When used according to the present invention against viruses, effective dose ranges of the proanthocyanidin polymers are about 5.0–about 30 mg/kg if given orally (P.O.), about 0.1–about 10 mg/kg if given intraperitoneally (I.P.), and about 5–about 30 mg/kg/day if given by aerosol. If given topically, the proanthocyanidin polymer is applied in a suitable vehicle at a concentration of about 5 to about 15%.

When administered to warm-blooded animals, including humans, the proanthocyanidins may be combined with water, an aqueous solution or any physiologically acceptable carrier or vehicle The following series of Examples are presented for purposes of illustration and not by way of limitation on the scope of the invention.

6. EXAMPLES

6.1 ISOLATION OF A NOVEL PROANTHOCYANIDIN POLYMER FROM A *CROTON LECHLERI* SPECIES (PROANTHOCYANIDIN POLYMER A

In one series of experiments, a novel proanthocyanidin polymer was obtained as follows:

*C. lechleri* trees were tapped and felled near the village of San Pablo de Cuyana on the Nanay River 100 kilometers from Iquitos, Peru. The latex was obtained over a period of 24 hours by scoring the trees.

The latex (1 l) obtained from the *Croton lechleri* trees was diluted with isopropanol in the ratio of 1 part latex to 3 parts isopropanol (3 l) and allowed to stand for 15 hours at 10° C. The resultant isopropanol-diluted latex was centrifuged, and the insoluble material was removed by decantation, leaving the mother liquor (3.7 l). The mother liquor was concentrated to dryness by rotoevaporation at 33° C. to give 240 g of a deep-red brown powder. This concentrated material (980 g) was subjected to gel filtration using Sephadex CM-50 with water (20 l) as the mobile phase. The early-eluting fractions containing a-red pigment were detected at λ 200–350 nm or by visual detection of a red band eluting through a transparent column. To isolate the proanthocyanidin polymer, the early-eluting fractions were collected and subjected to gel filtration chromatography and/or HPLC as described below.

The HPLC isolation was performed by injecting 5 μl of concentrated samples onto a Perkin-Elmer LC Analyst liquid chromatograph system equipped with an IC-200 autosampler, LC 600 pumps and a LC-235 diode array detector using a Waters Ultrahydrogel 500 GPC column with Burdick and Jackson HPLC-grade water at 0.8 ml/min at ambient temperature, with detection at λ 280 and 195 nm. The proanthocyanidin polymer was found to have a retention time of 4.6–5.6 minutes depending on sample concentration, column conditioning and temperature.

The red-pigment containing fractions isolated from Sephadex CM-50 were combined and subjected to gel filtration chromatography over Toyopearl HW-40S (2.5 L), using water, 10% acetone/water, 20% acetone/water, and finally 40% acetone/water in a step gradient fashion. The late-eluting red fractions detected by uv-vis as λmax 340 nm, were combined and concentrated for further purification on HPLC as described above. The combined fractions isolated from HPLC were again subjected to gel filtration chromatography over Toyopearl HW-40S to yield a proanthocyanidin polymer designated proanthocyanidin polymer A.

In another series of experiments, a novel proanthocyanidin polymer was obtained as follows:

Four liters of cold crude latex from the *C. lechleri* (or from the entire macerated plant, the bark or the roots) were diluted with twelve liters of isopropanol, stirred and stored at 5° C. for 15 hours. The residue was removed by filtration and the solution evaporated to dryness, in vacuo, yielding about 970 g. of solids.

The solids were added, with stirring, to 6 l of water and 3.6 l of n-butanol. The aqueous phase was separated and concentrated to dryness giving 700 g of material which was added, with stirring, to 2 l methanol, and then 12 l of ethyl acetate was added. The solution was kept at 15° for 15 hrs and the solid material removed by filtration and discarded. The solution was concentrated to dryness yielding approximately 390 g. of crude proanthocyanidin polymer A.

The proanthocyanidin polymer A fraction was concentrated by a combination of cation exchange, adsorption and size exclusion chromatography as follows: 450–600 g of the crude proanthocyanidin polymer A was passed through a CM-Sephadex C-50 pre-column using de-ionized water as the eluent. The orange and dark red fractions were collected and then chromatographed, using de-ionized water, over another Sephadex C-50 column equipped with a UV detector set at 460 nm, and 1–2 l fractions were collected. The initial pink band was discarded and the subsequent effluent passed through a column containing Sephadex G-50 until the broad red-brown band was eluted. 15% aqueous acetone was passed through the G-50 column until the effluent was colorless. Fractions of the effluent were examined by HPLC as described in Section 6.2, and those fractions containing proanthocyanidin polymer A were combined and evaporated to dryness yielding about 210 g. of proanthocyanidin polymer A.

6.2 PURIFICATION OF PROANTHOCYANIDIN POLYMER A

About 150 g. of crude proanthocyanidin polymer A, obtained as described in Section 6.1 above, was dissolved in 300 ml 20% aqueous acetone and was chromatographed over a mixed-mode gel-permeation/absorption column (Toyopearl HW40S, a spherical methyl methacrylate polymer of 40 μm particle size). 16 l were collected, then the eluting solvent was changed to 40% aqueous acetone and 8 more liters were collected, then the elution was continued with 4 l of 60% aqueous acetone. The fractions containing proanthocyanidin polymer A, as shown by HPLC (See Section 6.3), were combined and the solvent removed in vacuo yielding approximately 57 g. of solid.

Final purification was accomplished by a combination of adsorption and size-exclusion chromatography: 50–75 g. of the above solid were dissolved in 90% ethanol and introduced onto a column containing Sephadex LH-20 (a cross-linked dextran gel with hydroxypropyl groups attached by ether linkages to glucose units of the dextran chains). Elution was carried out using 10 l of 90% aqueous ethanol, then 15 l of 20% aqueous acetone, 5 l of 40% aqueous acetone, 5 l of 50% aqueous acetone and then 5 l of 60% aqueous acetone. Fractions were collected at 2 l intervals and assayed by HPLC. The fractions containing proanthocyanidin polymer A were combined and evaporated to dryness in vacuo at 35° giving 35 g. of pure proanthocyanidin polymer A.

For the HPLC, a 30 cm gel-permeation column for non-aqueous mobile phases was used in which the stationary phase is Polymer Laboratories PL-Gel 5 m 500Å (a divinylbenzene-polystyrene polymer, 5 μ particles, 500Å pore size). The HPLC system was equipped with a diode array detector that generates UV spectra, with the detector set at 280 nm.

Samples are dissolved in 95% aq THF, which is also the developing solvent. At a flow rate of 1 ml/min, the proanthocyanidin polymer A peak maximum has a retention time of 7.2±0.5 min.; proanthocyanidin polymer B has a retention time of 6.5±0.5 min, indicating that proanthocyanidin polymer B has a larger molecular weight than proanthocyanidin polymer A.

6.3 CHEMICAL IDENTIFICATION AND STRUCTURAL FEATURES OF THE PROANTHOCYANIDIN POLYMER A

In the infrared, the proanthocyanidin polymer A of the invention, obtained as described in Section 6.1 above, shows a very broad intense peak ranging from 3550–2500 and other peaks at 1612, 1449, 1348, 1202, 1144, 1107, 1068 and 1027 cm–1. See FIG. 1.

The 1H NMR spectrum in $D_2O$ (400 MHz 24° C.) exhibited very broad peaks at δ7.1, 6.9, 6.1, 4.7 and 2.8 ppm. See FIG. 2.

Ultraviolet-visible spectral analysis in $H_2O$ revealed broad peaks at λ 202, 235, (shoulder), 275, 305 (shoulder), 460 and trailing greater than 600 nm. Although the UV data of the present polymer closely resembles those of other known proanthocyanidins, the visible data are clearly different. The known proanthocyanidin monomers and polymers are colorless (λ 205, 240, 275 nm) and have no absorption in the visible range, whereas certain of the isolated novel proanthocyanidin polymer A of the present invention are colored and have a visible absorption at 460 nm. The color of the proanthocyanidin polymer suggests the presence of a flavylium moiety or moieties within the proanthocyanidin polymer. This is consistent with the visible spectroscopic data reported for closely related monomeric anthocyanins which contain the flavylium moiety (λ 460–560 nm). ;

The 13C NMR spectra of the proanthocyanidin polymer was obtained at 100 MHz in $D_2O$. The experiments performed were broad-band decoupled. As shown in FIG. 3, the 13C NMR spectrum in $D_2O$ exhibited very broad peaks at δ155(C-5, C-7, C-9), 145(C-3', C-5')*, 143(C-3', C-4'), 130(C-1', C'-1'*, C-4'*), 128(C-1'), 121(C-6), 116(C-2', C-5'), 109(C-8, C-2'*, C-6'*), 97(C-6), 82(C-2), 76(C-2), 73(C-3), and 38(C-4) ppm, for the *prodelphinidin B ring. The 13C NMR data suggest some key points of structural differences between the novel antiviral proanthocyanidin polymers of the present invention and known proanthocyanidin polymers. The most significant difference is a substantially larger peak in the region of 109 ppm for the proanthocyanidin polymers of this invention when compared with 13C NMR spectra of other proanthocyanidin polymers known in the literature (compare with spectra in Czochanska et al., 1979, *J.C.S. Chem. Comm.*, p. 375–77; in Harborne, J. B. and Mabry, T. J. ed., *The Flavonoids: Advances in Research*, Chapman and Hall, N.Y., 1982, pp. 51–132, incorporated herein by reference). The 13C NMR data of the polymer is indicative of the proanthocyanidin class of polymers. In particular, the 13C NMR chemical shift data of the isolated proanthocyanidin polymer (C-6'=132 ppm, C-2'= 115 pm, C-3' & C-4'=145 ppm, C-5'=116 ppm, C-6'-107 ppm, C-3' & C-5'=146 ppm, C-4'-133 ppm) is consistent with a polymer composed of procyanidin B ring moieties with the individual flavonol C ring units possessing both the 2,3-trans and 3,4-trans [similar to (+)-catechin; C-2=83 ppm, C-3=73 ppm, C-4=38 ppm] and 2,3-cis-3,4-trans [similar to (−)-epicatechin; C-2=77 ppm, C-3=73 ppm, C-4=73 ppm] stereochemistries. The present experiment data indicates that proanthocyanidin polymer A is comprised of catechin, epicatechin, gallocatechin and galloepicatechin. The HPLC data suggest that the average number of flavonoid units is about 7. The HPLC data also suggests that number of flavonoid units vary from 2 to 11.

The proanthocyanidin polymer A is soluble in methanol, water and aqueous solutions. The proanthocyanidin polymer A is soluble in water at concentrations of at least about 10 mg/ml. The polymer has lower solubility in normal saline and other salt solutions. Mass spectral analysis indicate that proanthocyanidin polymer A has a molecular weight average of about 2,100 daltons.

6.4 ISOLATION OF A PROANTHOCYANIDIN POLYMER FROM *CALOPHYLLUM INOPHYLUM* (PROANTHOCYANIDIN POLYMER B)

A novel proanthocyanidin polymer according to the present invention can be isolated by a method similar to that described above in Section 6.1 from the entire macerated plant, the bark, the leaves, the roots or the latex of *Calophyllum inophylum*. According to a preferred method, the proanthocyanidin polymer is obtained by the method described in Section 6.1, except that water is used as the preferred extraction solvent.

In one series of experiments, a novel proanthocyanidin polymer, designated proanthocyanidin polymer B, was obtained from *Calophyllum inophylum* latex.

2,849 g of the latex from *Calophyllum inophylum* was mixed with 12.4 l of a 1:1 mixture of isopropanol and water, stirred and stored at room temperature for 36 hours. The residue was removed by filtration and the solution was evaporated to dryness, in vacuo, giving 133.5 g of solids.

The solids were added, with stirring, to 30 g of methanol. The solution was then filtered away from the solids, and a 1:1 mixture of water and ethyl acetate was added. The water fraction was separated and n-butyl alcohol was added. The water fraction was separated from the alcohol fraction and concentrated to dryness yielding approximately 10.4 g of crude proanthocyanidin polymer B.

The crude proanthocyanidin polymer B was passed through a CM-50 Sephadex CC column using deionized water as the eluting solvent. A red band was collected and fractionated using a LH-20 CC column, eluted with 70% aqueous ethanol solution and 20%, 50% and 70% aqueous acetone solutions to give proanthocyanidin polymer B. At lower concentrations, a solution of proanthocyanidin polymer B is essentially colorless. At higher concentrations, the solution of proanthocyanidin polymer B is tan.

6.5 CHEMICAL IDENTIFICATION AND STRUCTURAL FEATURES OF THE PROANTHOCYANIDIN POLYMER B

The $^{13}C$ NMR spectrum of proanthocyanidin polymer B (FIG. 4) confirms that the polymer is a member of the class of proanthocyanidin polymers and comprises principally catechin and epicatechin monomeric flavonoid units. Gel permeation chromatography (GPC) indicates that proanthocyanidin polymer B has a molecular weight that is larger than proanthocyanidin polymer A. Consistent with the GPC data, HPLC-GPC retention time of proanthocyanidin polymer B is shorter than that for proanthocyanidin polymer A under the same conditions—again indicating the larger size of proanthocyanidin polymer B. HPLC indicates that polymer B has a molecular weight average of about 3000 daltons, corresponding to an average number of flavonoid units of about 10. The HPLC data also suggests that the number of flavonoid units vary from 5 to 16. Mass spectral analysis indicates that proanthocyanidin polymer A has a molecular weight average of about 2100 daltons.

The Fourier-transform infra-red spectrum of proanthocyanidin polymer B is quite similar to that of proanthocyanidin polymer A (See FIG. 5 and FIG. 1).

Likewise, the UV-visible spectrum of proanthocyanidin polymer B is similar to that of proanthocyanidin polymer A except for the absence of the peak at 460 nm.

7. SCREENING OF PROANTHOCYANIDIN POLYMER A FOR ANTIVIRAL ACTIVITY

In one series of experiments, proanthocyanidin polymer A was tested for antiviral activity against the following viruses: Respiratory syncytial virus subtype variants, A2-Tracey, A-Long, B-46791, B-47063 and B-18537; parainfluenza virus, type 3 (PIV-3); adenoviruses, type 5 and 7; influenza, A-Taiwan (H1N1); A-Leningrad (H3N2); A-Japan; A-Port Chalmbers; A-NWS33; B-USSR; B-Tama; B-RF; measles virus, and Edmonston strain.

All viruses were obtained from the Influenza Research Center, Baylor College of Medicine, Houston, Tex., with the exception of measles virus which was obtained from ATCC. For comparison, ribavirin was included in the screening assay.

The following procedure was used to assay for antiviral activity. Assays were performed in 96-well tissue culture plates. All dilutions and tissue culture suspensions were prepared in minimal essential medium containing antibiotics penicillin and streptomycin and 2% fetal calf serum (2% FCS-MEM). Test compounds (0.05 ml) were added in quadruplicate to wells of the test plates containing a subconfluent monolayer of HEp2 cells (ca. $3 \times 10^3$ cells). The compounds were diluted using serial 2-fold dilutions usually starting with a final concentration of 1 mg/ml. Approximately 100 median tissue culture infectious doses ($TCID_{50}$) of the appropriate test virus in 0.05 ml was added. Tissue control wells contained medium, without virus or antiviral compound, and antiviral control wells contained antiviral compound without virus. Ribavirin was included in each assay as a positive antiviral control, except for the adenoviruses where Ribavirin fails to demonstrate antiviral activity. Back titrations of each test virus were also included in each assay. All plates were incubated at 37° C. in a 5% $CO_2$ incubator. Virus control wells were observed daily. When these wells exhibited 80–100% cytopathic effect (CPE), all wells were observed for CPE. In addition to visual and microscopic observance of CPE, inhibition of syncytial formation was used to confirm activity against RSV.

In each antiviral assay, a 50% minimal inhibitory concentration ($ED_{50}$) was determined. The $ED_{50}$ was calculated by determining the median minimal concentration of compound tested in wells inhibiting CPE 50% compared to virus control wells. The actual calculation of the $ED_{50}$ value was done with the aid of the computer program, "Dose-effect analysis with microcomputers" of Chou et al., 1984, *Adv. Enz. Regul.*, 22:27–55.

The effect of each compound on the growth of uninfected tissue culture cells, seeded at low densities to allow rapid growth, was also evaluated. From this assay, a 50% minimal toxic concentration ($ID_{50}$) was determined. The assay for cell toxicity or inhibition of cell growth involved the following procedure. Test compounds (0.1 ml/well) were serially diluted 2-ofld. To the appropriate wells were added 0.1 ml of human HeLa, A549 or HEp2 cells, 0.1 ml of mouse L929 cells, 0.1 m of monkey Vero cells or 0.1 ml of canine MDCK cells. Approximately $3 \times 10^3$ cells were added to each well. Control wells consisted of wells containing a range of cell concentration (e.g., $3 \times 10^3$ cells, 1:2 dilution of this number, 1:4, 1:8 and 1:16) in medium without any antiviral compound. A vehicle control consisting of serial dilutions of whatever vehicle was used for a particular compound (e.g., 10% DMSO, 50% methanol) was also included in each assay in duplicate. All plates were incubated at 37° C. in a 5% $CO_2$ incubator. After control wells containing cells, but no test compound, reached confluency, 3-[4,5-Dimethylthiazol- 2-yl]-2,5-Diphenyltetrazolium Bromide (MTT) was added to all wells. Three hours later, acid alcohol (0.1 ml of 0.4N HCl in isopropyl alcohol) was added to each well to solubilize any precipitate formed in each well. Plates were read on a plate reader (UV MAX, Molecular Devices) to determine the optical densities in each well. The median concentration of antiviral compound in the last wells causing a 50% reduction in O.D. was determined and termed "$ID_{50}$".

All wells in the assay were also observed microscopically for inhibition of cell growth. The results are shown in Table 1.

TABLE 1

Effect of In Vitro Screening for Antiviral Activity with Proanthocyanidin Polymer A

| | $ED_{50}$ (µg/ml) | |
| --- | --- | --- |
| Virus | Proanthocyanidin Polymer A | Ribavirin |
| Experiment 1 | | |
| RSV | 8.5 | 4.0 |
| Parainfluenza virus 3 | >94 | 15.6 |
| Influenza A | 88 | 15.0 |
| Influenza B | 125 | 18.0 |
| Adenovirus | >125 | — |
| Rhinovirus | >125 | 125 |
| Measles | >125 | 31.3 |
| Experiment 2 | | |
| RSV | 17.2 | 24.2 |
| Parainfluenza virus | 38.3 | 15.7 |
| Influenza A | 31.3 | 14.3 |
| Influenza B | 125 | 18.0 |
| Adenovirus 5 | >250 | >1000 |
| Adenovirus 7 | >250 | >1000 |
| Rhinovirus | >125 | 125 |
| Measles | >125 | 31.3 |
| Experiment 3 | | |
| RSV | 12 | 31 |
| Parainfluenza virus 3 | 5 | 12 |
| Influenza A | 4 | 14 |
| Adenovirus 7 | >250 | >1000 |

In the first experiment of Table 1, the $ED_{50}$ for the proanthocyanidin polymer A was determined to be 8.5 µg/ml for RSV. This activity compares quite closely to ribavirin with a $ED_{50}$ determined to be 4.0 µg/ml for RSV. The $ID_{50}$ (an index of cell toxicity) of the proanthocyanidin polymer A was 94 µg/ml. In the second experiment of Table 1, the $ED_{50}$ for the proanthocyanidin polymer A was 17.2 µg/ml for RSV as compared to 24.2 for ribavirin, and the $ID_{50}$ was 250 µg/ml. In the third experiment of Table 1 the $ED_{50}$ for the proanthocyanidin polymer A was 12 µg/ml and the $ID_{50}$ was greater than 250 µg/ml.

The results of antiviral activity of the proanthocyanidin polymer A compared to ribavirin in each assay was determined by calculating the drug Selective Index (SI), defined as the ratio of $ID_{50}/ED_{50}$. The Selective Index of the proanthocyanidin polymer A for RSV was 11 and 14.5 and 21 in the three experiments.

Virus rating (VR) was obtained by averaging the sum of the CPE values (0 for no CPE; 4 for 100% CPE) assigned to treated, infected monolayers at each compound concentration. This average is subtracted from the average of the sum of the CPE values in an equal number of virus control wells. A further adjustment was made to reflect any observed cytotoxicity. Values for VR were assigned as follows: VR greater than 1, defined as definite anti-viral activity; a VR of 0.5–0.9, as moderate to questionable activity; a VR of 0.1–0.5, as slight activity. The slight activity could be attributable to cytotoxicity or cytopathic effects of the compound per se. The VR of the proanthocyanidin polymer A against RSV was 1.5, indicating definite anti-viral activity in these in vitro assays. Also, the proanthocyanidin polymer A demonstrated substantial anti-viral activity against parainfluenza and influenza A viruses in all three experiments.

In another series of experiments, polymer A was tested for antiviral activity against RSV, types A and B, influenza types A (Flu-A) and B (Flu-B), and parainfluenza types (PIV-1) and 3 (PIV-3).

The cell lines used were Human HeLa, A549 and HEp-2 cells, mouse L929 cells, monkey Vero cells, canine MDCK cells.

The effect of the proanthocyanidin polymer A on the viability and growth of cells was determined by measurement of mitochondrial respiration and expressed as a 50% minimal toxic concentration ($ID_{50}$). In this assay, as in the $ED_{50}$ assay, the proanthocyanidin polymer A was assayed in serial 2-fold dilutions in quadruplicate across 96-well microtitre plates. Again, wells were seeded at the low density of $3\times10^3$ cells per well to allow for rapid growth. Vehicle controls which consisted of serial dilutions of vehicle (which, in the case of proanthocyanidin polymer A, was water) were included in each assay in duplicate. Blanks which consisted of media alone and media plus drug were also included. All plates were incubated at 37° C. in a 5% $CO_2$ incubator until the tip concentration of cells in control wells reached confluency, usually 3 days. All wells in each assay were observed microscopically for cyctotoxicity. Then 0.05 ml of MTT (3-[4,5-dimethythiazole-2-yl]-2,5-diaphenyltetrazolium bromide)(5 mg/ml in PBS) was added to all wells and the incubation continued. Three hours later acid alcohol (0.05 ml of N HCl in isopropyl alcohol) was added to each well. The optical densities (O.D.) of each well were read at 490 nm using a plate reader (UV MAX, Molecular Devices). The percent viability of cells at each concentration of drug was calculated by dividing the mean of the O.D.'s of the drug treated wells (minus the mean of the drug blank) by the mean of the O.D.'s of control wells (minus the mean of the blank), and multiplying by 100. The effect of the vehicle on cell viability was similarly calculated. A dose response curve for the toxicity of proanthocyanidin polymer A was generated and the $ID_{50}$ determined.

The following procedure was used to assay for antiviral activity. Assays were performed in 96-well tissue culture plates. All dilutions and tissue culture suspensions were prepared in minimal essential medium containing antibiotics penicillin and streptomycin and 2% fetal calf serum (2% FCS-MEM). Test compounds (0.05 ml) were added in quadruplicate to wells of the test plates containing a subconfluent monolayer of HEp2 cells (ca. $3\times10^3$ cells). The compounds were diluted using serial 2-fold dilutions usually starting with a final concentration of 1 mg/ml. Approximately 100 median tissue culture infectious doses ($TCID_{50}$) of the appropriate test virus in 0.05 ml was added. Tissue control wells contained medium, without virus or antiviral compound, and antiviral control wells contained antiviral compound without virus. Ribavirin was included in each assay as a positive antiviral control, except for the adenoviruses where Ribavirin fails to demonstrate antiviral activity. Back titrations of each test virus were also included in each assay. All plates were incubated at 37° C. in a 5% $CO_2$ incubator. Virus control wells were observed daily. When these wells exhibited 80–100% cytopathic effect (CPE), all wells were observed for CPE. In addition to visual and microscopic observance of CPE, inhibition of syncytia formation was used to confirm activity against RSV.

In each antiviral assay, a 50% minimal inhibitory concentration ($ED_{50}$) was determined. The $ED_{50}$ was calculated by determining the median minimal concentration of compound tested in wells inhibiting CPE 50% compared to virus control wells. The actual calculation of the $ED_{50}$ value was done with the aid of the computer program, "Dose-effect analysis with microcomputers" of Chou et al., 1984, *Adv. Enz. Regul.*, 22:27–55.

The selective index for proanthocyanidin polymer A was then calculated as the ratio of the $ID_{50}$ over the $ED_{50}$.

The results are shown in Tables 2–6. The results indicate that proanthocyanidin polymer A is as effective as ribavirin for inhibiting growth of RSV-A and B, PIV-1, PIV-3, FLU-A and FLU-B in vitro. The selective index values indicate low cytotoxicity for proanthocyanidin polymer A.

TABLE 2

Effect of Proanthocyanidin Polymer A and Ribavirin Against RSV.

| EXP # | PROANTHOCYANIDIN POLYMER A (µg/ml) | | | RIBAVIRIN (µg/ml) | | |
|---|---|---|---|---|---|---|
| | $ED_{50}$ | $ID_{50}$ | S.I. | $ED_{50}$ | $ID_{50}$ | S.I. |
| A-Tracy | 9.0 | 94.0 | 10.4 | 4.0 | 1000.0 | 250.0 |
| A-Tracy | 6.0 | 750.0 | 125.0 | 1.0 | 1000.0 | 83.3 |
| A-Tracy | 16.0 | 750.0 | 46.0 | 6.0 | 1000.0 | 166.7 |
| A-Long | 8.0 | 125.0 | 15.6 | 8.0 | 1000.0 | 125.0 |
| A-Long | 31.0 | 250.0 | 8.1 | 31.0 | 1000.0 | 32.3 |
| A-Long | 12.0 | 250.0 | 20.8 | 31.0 | 1000.0 | 32.3 |
| A-Long | 25.0 | 78.0 | 3.1 | 3.0 | 403.0 | 134.3 |
| A-Tracy | 2.0 | 94.0 | 47.0 | 12.0 | 1000.0 | 83.3 |
| B-46791 | 6.0 | 188.0 | 31.0 | 8.0 | 1000.0 | 125.0 |
| B-47063 | 6.0 | 98.0 | 16.3 | 12.0 | 1000.0 | 83.3 |
| B-18537 | 8.0 | 188.0 | 23.5 | 4.0 | 1000.0 | 250.0 |
| MEAN | 11.7 | 260.5 | 31.6 | 11.9 | 945.7 | 124.1 |
| S.E.M | 2.7 | 75.3 | 10.3 | 4.0 | 54.3 | 22.5 |

TABLE 3

Effect of Proanthocyanidin Polymer A and Ribavirin Against FLU-A.

| EXP # | PROANTHOCYANIDIN POLYMER A (µg/ml) | | | RIBAVIRIN (µg/ml) | | |
|---|---|---|---|---|---|---|
| | $ED_{50}$ | $ID_{50}$ | S.I. | $ED_{50}$ | $ID_{50}$ | S.I. |
| A-Taiwan | 16.0 | 750.0 | 46.9 | 8.0 | 1000.0 | 125.0 |
| A-Taiwan | 4.0 | 750.0 | 187.5 | 6.0 | 1000.0 | 166.7 |
| A-Taiwan | 12.0 | 750.0 | 62.5 | 23.0 | 1000.0 | 43.5 |
| A-Taiwan | 2.0 | 63.0 | 31.5 | 12.0 | 1000.0 | 83.3 |
| A-Taiwan | 0.8 | 250.0 | 312.5 | 7.8 | 1000.0 | 128.2 |
| A-Taiwan | 4.0 | 25.0 | 6.3 | 7.8 | 1000.0 | 128.2 |
| A-Shanghai | 0.8 | 187.0 | 233.8 | 6.0 | 1000.0 | 83.3 |
| A-Leningrad | 4.0 | 750.0 | 187.5 | 6.0 | 1000.0 | 166.7 |
| B-NWS/33 | 8.0 | 41.0 | 5.1 | 1.0 | 100.0 | 100.0 |
| B-Japan | 12.0 | 24.0 | 2.0 | 1.6 | 78.0 | 48.8 |
| B-Portchalm | 13.0 | 35.0 | 2.7 | 1.0 | 68.0 | 68.0 |
| MEAN | 7.0 | 263.5 | 81.5 | 8.2 | 749.6 | 101.9 |
| S.E.M | 1.6 | 96.7 | 33.2 | 2.0 | 129.3 | 13.3 |

TABLE 4

Effect of Proanthocyanidin Polymer A and Ribivarin Against FLU-B.

| EXP # | PROANTHOCYANIDIN POLYMER A (µg/ml) | | | RIBAVIRIN (µg/ml) | | |
|---|---|---|---|---|---|---|
| | $ED_{50}$ | $ID_{50}$ | S.I. | $ED_{50}$ | $ID_{50}$ | S.I. |
| B-Yamagata | 3.0 | 187.0 | 62.3 | 6.0 | 1000.0 | 166.7 |
| B-Yamagata | 1.5 | 187.0 | 124.7 | 8.0 | 1000.0 | 125.0 |
| B-USSR | 62.0 | 750.0 | 12.1 | 4.0 | 1000.0 | 250.0 |
| B-USSR | 0.8 | 250.0 | 312.5 | 7.8 | 1000.0 | 128.2 |
| B-USSR | 3.0 | 250.0 | 83.3 | 7.8 | 1000.0 | 128.2 |
| B-HongKong | 11.0 | 35.0 | 3.2 | 1.0 | 80.0 | 80.0 |
| MEAN | 13.6 | 275.5 | 99.7 | 5.8 | 846.7 | 146.3 |

TABLE 4-continued

Effect of Proanthocyanidin Polymer A
and Ribivarin Against FLU-B.

| EXP # | PROANTHOCYANIDIN POLYMER A (µg/ml) | | | RIBAVIRIN (µg/ml) | | |
|---|---|---|---|---|---|---|
|  | $ED_{50}$ | $ID_{50}$ | S.I. | $ED_{50}$ | $ID_{50}$ | S.I. |
| S.E.M | 9.8 | 100.0 | 46.4 | 1.1 | 153.3 | 23.6 |

TABLE 5

Effect of Proanthocyanidin Polymer A
and Ribavirin Against PIV-1.

| EXP # | PROANTHOCYANIDIN POLYMER A (µg/ml) | | | RIBAVIRIN (µg/ml) | | |
|---|---|---|---|---|---|---|
|  | $ED_{50}$ | $ID_{50}$ | S.I. | $ED_{50}$ | $ID_{50}$ | S.I. |
| PIV-1 | 0.8 | 125.0 | 166.7 | 12.0 | 1000.0 | 83.3 |
| PIV-1 | 2.0 | 187.0 | 93.5 | 12.0 | 1000.0 | 83.3 |
| PIV-1 | 6.0 | 750.0 | 125.0 | 8.0 | 1000.0 | 125.0 |
| MEAN | 2.9 | 354.0 | 124.9 | 10.7 | 1000.0 | 97.2 |
| S.E.M | 1.6 | 198.8 | 18.1 | 1.3 | 0.0 | 13.9 |

TABLE 6

Effect of Proanthocyanidin Polymer A
and Ribavirin Against PIV-3.

| EXP # | PROANTHOCYANIDIN POLYMER A (µg/ml) | | | RIBAVIRIN (µg/ml) | | |
|---|---|---|---|---|---|---|
|  | $ED_{50}$ | $ID_{50}$ | S.I. | $ED_{50}$ | $ID_{50}$ | S.I. |
| PIV-3 | 94.0 | 124.0 | 1.3 | 16.0 | 1000.0 | 62.5 |
| PIV-3 | 250.0 | 750.0 | 3.0 | 46.0 | 1000.0 | 21.7 |
| PIV-3 | 93.0 | 125.0 | 1.3 | 8.0 | 1000.0 | 125.0 |
| PIV-3 | 16.8 | 250.0 | 15.6 | 16.0 | 1000.0 | 62.5 |
| PIV-3 | 5.0 | 250.0 | 50.0 | 8.0 | 1000.0 | 125.0 |
| PIV-3 | 84.0 | 78.0 | 0.9 | 8.0 | 1000.0 | 125.0 |
| PIV-3 | 8.0 | 188.0 | 23.5 | 6.0 | 1000.0 | 166.7 |
| MEAN | 78.6 | 252.1 | 13.7 | 15.4 | 1000.0 | 98.3 |
| S.E.M | 32.4 | 86.6 | 6.9 | 5.3 | 0.0 | 19.0 |

Fractions of proanthocyanidin polymer A have been further purified by HPLC using a GPC column and standards. Specifically, two fractions have been isolated: one fraction having a molecular weight average of 700 daltons (corresponding to 2 to 3 flavonoid monomeric units) and the second fraction having a molecular weight average of 3000 daltons (corresponding to 9 to 11 flavonoid monomeric units). The two fractions show essentially the same chemical shifts in the $^{13}C$ and $^{1}H$ NMR spectra as the unfractionated proanthocyanidin polymer A.

In vitro experiments indicate both fractions are active against RSV. The fraction having an average of 2 to 3 flavonoid units has an in vitro RSV antiviral activity of $ED_{50}$=10 µg/ml, while the second fraction having an average of 9–11 flanonoid units has an $ED_{50}$=40 µg/ml.

8. EFFECTIVENESS OF PROANTHOCYANIDIN POLYMER A FOR TREATMENT OF RSV

In vivo and in vitro assays indicate that the novel proanthocyanidin polymer A of the invention is a useful therapeutic agent for the treatment of RSV infections. The present invention provides a safer therapeutic treatment for RSV infections without the toxic effects associated with Ribavirin, the currently approved composition for treatment of such infections.

Hispid Cotton Rats were innoculated with RSV A2 intranasally on day 1 and given an intraperitoneal dose of 0.1–30.0 mg/kg of the proanthocyanidin polymer prepared in distilled water on day 2, 3 and 4. Control animals received an equal volume of distilled water. In one experiment, as a comparison, a dose of 10–90 mg/kg of Ribavirin was used. All animals were killed on day 5. Lungs were removed and washed via transpleural lavage. The fluid collected was assessed for RSV titer in a microtiter assay using HEp2 cells.

Assays were performed in 96-well tissue culture plates. All dilutions and tissue culture suspensions were prepared in minimal essential medium containing antibiotics and 5% fetal calf serum (5% FCS-MEM). Lung lavage fluid was added in quadruplicate to wells of the test plates containing a subconfluent monolayer of cells (ca. $3\times10^3$ cells). Approximately 100 median tissue culture infectious doses ($TCID_{50}$) of the appropriate test virus in 0.05 ml was added. Tissue control wells contained medium, but no virus. All plates were incubated at 37° C. in a 5% $CO_2$ incubator. Virus control wells were observed daily. When these wells exhibited 80–100% CPE, all wells were observed for CPE. In addition to visual CPE, inhibition of syncytia formation is used to confirm activity against RSV. Lung RSV titer $log_{10}$ was calculated as described by Dubovi et al., 1983; 1984. The results are shown in Tables 7–8.

As shown in Table 7, for each experiment, the proanthocyanidin polymer A demonstrated a dose-dependent decrease in RSV titer compared to controls. This indicates that the proanthocyanidin polymer A has effective antiviral activity against RSV in vivo. As shown in Table 8, direct comparison of the antiviral effect of the procyanidin polymer A to ribavirin (intraperitoneal administration) demonstrates that the polymer composition of the invention is significantly more potent that ribavirin, the drug currently used to treat RSV infections.

Hispid Cotton Rats were inoculated with RSV A2 intranasally on day 1 and given an oral dose of 1.0–10.0 mg/kg of the proanthocyanidin polymer on days 2, 3 and 4. All animals were killed on day 5 and lung tissues were collected. Lungs were removed and washed via transpleural lavage. The fluid collected was assessed for RSV titer in a microtiter assay using HEp2 cells as described above. Results are shown in Table 9.

As shown in Table 9, the proanthocyanidin polymer administered orally significantly lowered RSV titers at 10 mg/kg compared to controls. This indicates that the proanthocyanidin polymer has effective antiviral activity when administered orally against RSV and is more active than ribavirin.

TABLE 7

Effect of Proanthocyanidin Polymer A Against
RSV Infection of Cotton Rats, Intraperitoneal Dosing

| Treatment (Mg/Kg) | Lung titer$_a$ | P |
|---|---|---|
| EXPERIMENT #1 | | |
| Control | 3.98 ± 0.14 (9549) | — |
| 0.1 | 3.78 ± 0.31 (6025) 36.9% kill | 0.08 |
| 0.3 | 3.21 ± 0.05 (1621) 83.0% kill | 0.05 |

TABLE 7-continued

Effect of Proanthocyanidin Polymer A Against
RSV Infection of Cotton Rats, Intraperitoneal Dosing

| Treatment (Mg/Kg) | Lung titer[a] | P |
|---|---|---|
| 1.0 | 3.28 ± 0.65 (1905) 80.1% kill | 0.04 |
| EXPERIMENT #2 | | |
| Control | 4.3 ± 0.8 (20,000) | — |
| 1.0 | 3.1 ± 0.5 (1258) 94% kill | 0.08 |
| 3.0 | 3.4 ± 0.5 (2,511) 87% kill | 0.05 |
| 10.0 | 3.6 ± 0.3 (3,981) 80% kill | 0.06 |
| EXPERIMENT #3 | | |
| Control | 3.98 ± 0.14 (9,549) | — |
| 3.0 | 4.00 ± 0.02 (10,000) 0% kill | n.s. |
| 10.0 | 3.88 ± 0.3 (7,585) 20.6% kill | n.s. |
| 30.0 | 3.70 ± 0.28 (5,011) 47.5% kill | n.s. |
| EXPERIMENT #4 | | |
| Control | 5.22 ± 0.27 (165,958) | — |
| 0.1 | 4.87 ± 0.32 (74,131) 55.3% kill | n.s. |
| 0.3 | 4.25 ± 0.39 (17,782) 89.3% kill | 0.014 |
| 1.0 | 4.27 ± 0.5 (18,620) 88.8% kill | 0.046 |
| 3.0 | 4.41 ± 0.19 (25,703) 84.5% kill | 0.012 |
| EXPERIMENT #5 | | |
| Control | 4.5 ± 0.2 (31,622) | — |
| 10 | 4.5 ± 0.2 (31,622) 0% kill | n.s. |
| 30 | 4.0 ± 0.3 (10,000) 68.4% kill | 0.03 |
| 90 | 2.8 ± 0.3 (631) 98% kill | <0.0001 |

[a]Lung titer represents: RSV titer $\log_{10}$/g lung (Mean ± S.D.)

TABLE 8

Effect of Proanthocyanidin Polymer A and Ribavirin
Against RSV Infection of Cotton Rats, Intraperitoneal Dosing

| | Lung titer[a] | P |
|---|---|---|
| Proanthocyanidin Polymer (Mg/Kg) | | |
| Control | 5.22 ± 0.27 (165,958) | — |
| 0.1 | 4.87 ± 0.32 (74,131) 55.33% Kill | n.s. |
| 0.3 | 4.25 ± 0.39 (17,782) 89.29% Kill | 0.014 |
| 1.0 | 4.27 ± 0.5 (18,620) 88.78% Kill | 0.046 |
| 3.0 | 4.41 ± 0.19 (25,703) 84.51% Kill | 0.012 |
| Ribavirin (Mg/Kg) | | |
| Control | 4.5 ± 0.2 (31,622) | — |
| 10 | 4.5 ± 0.2 (31,622) 0% Kill | n.s. |
| 30 | 4.0 ± 0.3 (10,000) 68.4% Kill | 0.03 |
| 90 | 2.8 ± 0.3 (631) 98% Kill | <0.0001 |

[a]Lung titer represents: RSV titer $\log_{10}$/g lung (Mean ± S.D.)

TABLE 9

Effect of Oral Proanthocyanidin Polymer A
Against RSV Infection of Cotton Rats

| Treatment (Mg/Kg) | Lung titer[a] | P |
|---|---|---|
| EXPERIMENT #1 | | |
| Control | 4.45 ± 0.50 (28,183) | — |
| 1.0 | 3.62 ± 0.42 (4168) 85.7% kill | 0.045 |
| 3.0 | 4.22 ± 0.23 (16,595) 41.1% kill | n.s. |
| 10.0 | 3.95 ± 0.48 (8912) 68.4% kill | n.s. |
| EXPERIMENT #2 | | |
| Control | 3.86 ± 0.55 (7,244) | — |
| 1.0 | 3.60 ± 0.01 (3,981) 45.0% kill | n.s. |
| 3.0 | 3.71 ± 0.50 (5,129) 29.2% kill | n.s. |
| 10.0 | 2.90 ± 0.57 (794) 89.0% kill | 0.06 |
| EXPERIMENT #3 | | |
| Control | 3.90 ± 0.3 (7,943) | — |
| 1.0 | 3.90 ± 0.8 (7,943) 0.0% Kill | n.s. |
| 3.0 | 4.00 ± 0.8 (10,000) 0.0% Kill | n.s. |
| 10.0 | 2.90 ± 0.5 (794) 92% Kill | 0.01 |
| Ribavirin (40 mg/kg) | 3.30 ± 0.5 (1,995) 80% Kill | 0.07 |

[a]Lung titer represents RSV titer $\log_{10}$/g lung (Mean ± S.D.)

An additional series of experiments conducted as described above confirms the in vivo activity of polymer A against RSV.

Proanthocyanidin polymer A displayed a mean $ED_{50}$ value of 1.52±0.62 mg/kg following 3-day i.p. administration, and 3.6±1.66 mg/kg following 3-day p.o. administration. See Table 10. The reference antiviral agent, ribavirin, displayed $ED_{50}$ values of 40±6, and >90 mg/kg following i.p. and p.o. administration, respectively. Proanthocyanidin polymer A at a dose of 10 mg/kg p.o. resulted in a 68–92% reduction in lung RSV titers following oral administration, and a 21–80% reduction following i.p. administration. Ribavirin (40 mg/kg) resulted in a >90% reduction in lung titers following oral administration, and a 50% reduction following i.p. administration.

TABLE 10

Effect of Proanthocyanidin Polymer A
Against RSV infection of Hispid Cotton Rats:

| Exp. # | $ED_{50}$ (mg/kg) | |
|---|---|---|
| | Proanthocyanidin Polymer A | Ribavirin |
| 3-Day Intraperitoneal Dosing | | |
| 1 | 1.0 | 40 |
| 2 | 0.3 | 30 |
| 3 | 3.0 | 50 |
| 4 | 0.3 | |
| 5 | 3.0 | |
| Mean ± S.E.M. | 1.52 ± 0.62 | 40 ± 5.8 |
| 3-Day Oral Dosing | | |
| 1 | 3.0 | >90 |
| 2 | 1.0 | >90 |
| 3 | 10.0 | |
| 4 | 3.0 | |
| 5 | 1.0 | |
| Mean ± SEM | 3.6 ± 1.66 | >90 |

In vivo experiments have also been performed to study the effect of proanthocyanidin polymer A upon course of respiratory syncytial virus infection in African green monkeys.

Proanthocyanidin polymer A was weighed out in 25 mg aliquots and refrigerated as the dry powder until use. Glucose was prepared as a 0.5% solution and refrigerated. A 25 mg sample of proanthocyanidin polymer A was dissolved in 50 ml 0.5% glucose daily and the solution sterilized by filtration through a 0.22 µm membrane filter. Subsequent dilutions were made in 0.5% glucose from the 0.5 mg/ml solution at 1:2 and 1:5 to give concentrations of 0.25 mg/ml and 0.1 mg/ml respectively.

Groups of three monkeys were dosed with proanthocyanidin polymer A at 0.5 mg/kg, 0.25 mg/kg or 0.1 mg/kg by administering the drug at 1 ml per kg of body weight by intravenous injection. The time of administration of the drug infusion to each monkey was approximately 1 minute. A control group of three monkeys received 1 ml of the 0.5% glucose solution.

Four hours after the initial treatment with proanthocyanidin polymer A, each of the monkeys was infected with a $10^{-2}$ dilution of stock respiratory syncytial virus. The titer of the stock virus was $1 \times 10^5$ $TCID_{50}$/ml. Each monkey received 1 ml of the $10^{-2}$ virus dilution by intratracheal inoculation and 1 ml applied drop-wise to external nares. The total virus dose therefore was $2 \times 10^3$ $TCID_{50}$/monkey. Treatment with proanthocyanidin polymer A was administered again 8 hours later resulting in daily doses of proanthocyanidin polymer A of 1.0, 0.5, and 0.2 mg/kg with three monkeys per group. Twice daily treatment continued at 8 a.m. and 8 p.m. for a total of seven days.

To determine virus shedding throat swabs were taken daily each morning prior to treatment with proanthocyanidin polymer A using a dacron nasal-pharyngeal swab. The swab was placed in 1.0 ml of tissue culture (minimum essential medium with a 10% fetal bovine serum and penicillin, streptomycin and fungizone). Titrations were performed on the throat swab solutions by preparation of ten-fold dilutions which were inoculated into duplicate wells of BSC-40 cells grown in 24-well plates. Following incubation at 37° C. in a $CO_2$ incubator the titer of each specimen was determined by microscopic examination for viral cytopathology and the titer expressed as the $log_{10}$ of the $TCID_{50}$ per ml. At the time of each morning specimen collection each monkey was examined for rhinorrhea and other respiratory symptoms including coughing, sneezing and signs of respiratory distress. The animal attendant would also note any coughing or sneezing during routine daily care of the monkeys. Fourteen days after virus inoculation each of the monkeys was bled and the sera tested for antibody titers in a neutralization assay against approximately 100 $TCID_{50}$ of respiratory syncytial virus.

The results of intravenous dosing with proanthocyanidin polymer A are summarized in Table 11. Each of the three control monkeys became infected with respiratory syncytial virus, shedding virus in the oropharynx for 7 to 10 days or longer. Virus titers reached five and six $logs_{10}$ in two of the three control monkeys and 3.5 $log_{10}$ in the third. In the monkeys receiving proanthocyanidin polymer A at the highest dose of 1 mg/kg/day, the time of virus shedding and titers of virus shed were much reduced. One monkey shed virus for one day, a second for three days, and a third for four days. In one monkey, the maximum virus titer was two logs. The mid dose of 0.5 mg/kg/day was also seen to shorten the time of shedding in two monkeys with the third monkey excreting virus in the oropharynx for nine days. Virus titers were generally lower although maximum titers of four logs were detected in two of the three monkeys and three logs in the third. A minimal effect was seen at the lowest dose of 0.2 mg/kg/day. Virus shedding was seen for six or seven days and a maximum titers of three $logs_{10}$ were seen in two monkeys and five logs in the third monkey. Antibody titers to respiratory syncytial virus were detected in all monkeys at 14 days with titers of 1:40 to 1:160.

Daily mean $log_{10}$ titers are presented for each treatment group (See Table 12). Mean titers were lower in each of the three treatment groups when compared with the mean titers in the control group on each of the sampling days. The mean titers were considerably reduced in the 1.0 mg/kg/day treatment group, and a dose related reduction is also seen in the other two groups.

Clinical symptoms were more prevalent in the control monkeys than in the monkeys treated with proanthocyanidin polymer A (See Table 13). Rhinorrhea is the most easily observed symptom and was seen in each of the three controls. No signs of toxicity were observed during daily examinations of the monkeys at the time of sampling or during daily inspection during the course of the study.

TABLE 11

Effect of Intravenous Dosing With Proanthocyanidin Polymer A Upon the Development of Respiratory Syncytial Virus Infection in African Green Monkeys.

| Treatment Group | Mnky # | Log$_{10}$ of Titer From Throat Swabs - Days Post-Infection (P.I.) 1 | 2 | 3 | 4 | 5 | 6 | 7 | 8 | 9 | 10 | AB Titer 14 Days P.I |
|---|---|---|---|---|---|---|---|---|---|---|---|---|
| Control | K349 | <1.0 | <1.0 | 1.0 | 2.5 | 2.0 | 3.0 | 3.5 | 2.5 | 1.0 | <1.0 | 1:80 |
| 0.5% Dex. | K553 | <1.0 | 1.0 | 3.0 | 4.0 | 5.0 | 5.0 | 6.0 | 4.5 | 2.0 | 0.5 | 1:160 |
| b.i.d., i.v. | K340 | <1.0 | 2.5 | 3.0 | 4.0 | 5.0 | 4.0 | 4.0 | 5.0 | 3.0 | 3.0 | 1:160 |
| 0.2 | K152 | <1.0 | <1.0 | <1.0 | 2.0 | 1.5 | 3.0 | 2.5 | 2.5 | 1.0 | 2.0 | 1:40 |
| mg/kg/day | H549 | <1.0 | <1.0 | 3.0 | 3.0 | 4.0 | 5.0 | 4.0 | 3.0 | <1.0 | <1.0 | 1:80 |
| b.i.d., i.v. | K100 | <1.0 | <1.0 | <1.0 | 1.5 | 1.0 | 3.0 | 2.0 | 1.0 | 0.5 | <1.0 | 1:80 |
| 0.5 | K154 | <1.0 | <1.0 | <1.0 | <1.0 | 2.0 | 1.5 | 3.0 | 4.0 | <1.0 | <1.0 | 1:40 |
| mg/kg/day | K332 | <1.0 | 0.5 | 1.0 | 2.0 | 3.0 | 3.0 | 3.0 | 4.0 | 3.0 | 1.0 | 1:80 |
| b.i.d., i.v. | K155 | <1.0 | <1.0 | <1.0 | 1.5 | 3.0 | 2.0 | 2.0 | 2.5 | <1.0 | <1.0 | 1:80 |
| 1.0 | K153 | <1.0 | <1.0 | <1.0 | <1.0 | <1.0 | <1.0 | 1.0 | <1.0 | <1.0 | <1.0 | 1:160 |
| mg/kg/day | K113 | <1.0 | <1.0 | <1.0 | <1.0 | 1.0 | 1.0 | 2.0 | 1.0 | <1.0 | <1.0 | 1:160 |
| b.i.d., i.v. | K350 | <1.0 | <1.0 | <1.0 | <1.0 | <1.0 | <1.0 | 0.5 | 1.5 | <1.0 | <1.0 | 1:80 |

TABLE 12

Mean Titers of RSV in Throat Swabs From African Green Monkeys Treated With Proanthocyanidin Polymer A.

| Treatment Group | Log$_{10}$ Mean Titer of RSV in Throat Swabs (Days P.I.) N = 3: 1 | 2 | 3 | 4 | 5 | 6 | 7 | 8 | 9 | 10 |
|---|---|---|---|---|---|---|---|---|---|---|
| Control | <1.0 | 1.2 | 2.3 | 3.5 | 4.0 | 4.0 | 4.5 | 4.0 | 2.0 | 1.2 |
| 0.2 mg/kg/day | <1.0 | <1.0 | 1.0 | 2.2 | 2.2 | 3.7 | 2.8 | 2.2 | 0.5 | 0.7 |
| 0.5 mg/kg/day | <1.0 | 0.2 | 0.3 | 1.2 | 2.7 | 2.2 | 3.0 | 3.2 | 1.0 | 0.3 |
| 1.0 mg/kg/day | <1.0 | <1.0 | <1.0 | <1.0 | 0.3 | 0.7 | 1.2 | 0.8 | <1.0 | <1.0 |

TABLE 13

Symptoms of Respiratory Syncytial Virus Infection in African Green Monkeys Treated With Proanthocyanidin Polymer A.

| Treatment Group | Monkey Number | Days of Symptoms During 10 Days: Rhinorrhea | Sneezing | Coughing |
|---|---|---|---|---|
| Control | K349 | 1 | — | 1 |
| 0.5% Dex | H553 | 2 | 3 | — |
| b.i.d., i.v. | K340 | 2 | 6 | 1 |
| 0.2 mg/kg/day | K152 | 2 | — | — |
| b.i.d., i.v. | K549 | 1 | 3 | — |
| | K100 | — | — | — |
| 0.5 mg/kg/day | K154 | — | 1 | — |
| b.i.d., i.v. | K332 | — | — | — |
| | K155 | — | — | — |
| 1.0 mg/kg/day | K153 | 2 | — | — |
| b.i.d., i.v. | K113 | — | — | — |
| | K350 | — | — | |

In summary, proanthocyanidin polymer A was seen to have a definite beneficial effect on respiratory syncytial virus infection in African green monkeys. A dose of 1.0 mg/kg given by intravenous injection twice daily resulted in shorter duration of virus shedding from the oropharynx, reduced titers of virus shed and reduced clinical symptoms. A dose of 0.5 mg/kg administered twice daily was also effective in reducing all three parameters of infection although to a lesser degree than was observed at the higher dose.

9. EFFECTIVENESS OF PROANTHOCYANIDIN POLYMER A FOR TREATMENT OF INFLUENZA A

Male and female BALB/c mice were used in in vivo tests to study the effectiveness of proanthocyanidin polymer A against Influenza A. The mice weighed 13–16 g and were obtained from Simonsen Laboratories (Gilroy, Calif.). They were quarantined 24 hr prior to use, and maintained on Wayne Lab Blox and tap water. Once the animals were infected, 0.006% oxytetracycline (Pfizer, New York, N.Y.) was added to the drinking water to control possible secondary bacterial infections.

Influenza A/NWS/33 (H1N1) was obtained from K. W. Cochran, University of Michigan (Ann Arbor, Mich.). A virus pool was prepared by infecting confluent monolayers of Madin Darby canine kidney (MDCK) cells, incubating them at 37° C. in 5% $CO_2$, and harvesting the cells at 3 to 5 days when the viral cytopathic effect was 90 to 100%. The virus stock was ampuled and stored at −80° C. until used.

The proanthocyanidin polymer A was dissolved in sterile water for injection (WFI) each day at the appropriate concentrations and used immediately. 1-Adamantanamine HCL (amantadine) was purchased from Sigma (St. Louis, Mo.) and was dissolved in sterile saline. 1-β-D-Ribofuranosyl-1,2,4-triazole-3-carboxamide (ribavirin) was purchased from ICN Pharmaceuticals, Inc. (Costa Mesa, Calif.) and was dissolved in sterile saline.

An Ohmeda Blox 3740 pulse oximeter (Ohmeda, Louisville, Ohio) with ear probe attachment was used.

Each mouse lung was homogenized and varying dilutions assayed in triplicate for infectious virus in MDCK cells as described by Sidwell, RW, Huffman JH, Call E. W., Alghamandan H., Cook P. D., Robins, R. K. "Effect of Selenazofurin on Influenza A and B Virus Infections in Mice", *Antiviral Res.*, 6:343–53 (1986).

Two experiments were conducted as follows:

Experiment 1: Seventeen male and seventeen female mice were infected intranasally (i.n.) with an approximate 90% lethal dose of virus (0.06 ml). This viral inoculum was equivalent to an approximately $10^5$ cell culture 50% infectious doses in MDCK cells. Treatment with 30, 10 or 3 mg/kg/day of proanthocyanidin polymer A or 125 mg/kg/day of amantadine was begun 2 days pre-virus exposure and continued once daily for 8 days. Pulse oximeter readings of arterial oxygen saturation ($SaO_2$) were determined on 5 male and 5 female mice daily through 10 days post-virus exposure and again on days 14 and 21. On infection days 2, 4, 6, 8, 10, 14 and 21, 3 mice (2 male, 1 female or 2 female, 1 male) were killed and their lungs removed, graded for consolidation, and frozen for laser assay of virus titer. Consolidation was scored from 0 (normal) to 4 (100% consolidation). The same animals used for $SaO_2$ determinations were held for 21 days and deaths noted as they occurred. As toxicity controls, 3 male and 3 female sham-infected mice were treated concomitantly with each dosage level of test compound. These animals together with normal untreated mice were weighed immediately prior to treatment and 18 hr after the final treatment.

Experiment 2: This experiment was identical to Experiment 1, except therapy began 4 hr post-virus exposure.

Statistical Evaluation: Increase in survivor number was evaluated using chi square analysis with Yate's correction. Mean survival time increases, virus titer and $SaO_2$ value differences were analyzed by t-test. Lung consolidation scores were evaluated by ranked sum analysis. The Exstatix™ program run on a Macintosh II computer was used to determine±standard errors (S.E.).

An overview of the results of these experiments is shown in Tables 14 and 15. The overview of the two experiments shows mean data compiled from all time points in which assays were made. The toxicity controls for these experiments indicated the 30 mg/kg/day dose of proanthocyanidin polymer A was toxic to the mice.

Experiment 1 (Early treatment initiation): The summary of Experiment 1 (Table 14) indicates significant influenza disease-inhibitory effects of the 30 and 10 mg/kg/day dosages of proanthocyanidin polymer A based on the reduction of lung consolidation. The $SaO_2\%$ were significantly increased in the infected female mice receiving the 10 and 3 mg/kg/day doses.

Amantadine was intended as a positive control in these experiments. Amantadine did not appear significantly effective in this experiment. However, it has been subsequently learned that this particular influenza virus is resistant to Amantadine.

More detailed examination of these parameters can be seen in FIGS. 6–9 for Experiment 1. Lung consolidation (FIG. 6) was particularly inhibited on the early sampling days; the consolidation gradually increased in all groups through the remainder of the experiment, but never reached the level of the virus controls.

Lung virus titers (FIG. 10) were not reduced early in the study, but by day 8 and 10, significant reductions were seen in mice treated with the 10 and 3 mg/kg/day dosages of proanthocyanidin polymer A.

The $SaO_2$ data were separated for male and female mice, since 5 animals of each sex were used for these determinations. Essentially no inhibition of $SaO_2$ decline was seen in male mice treated with either compound (FIG. 12). The female mice appeared to respond better, however (FIG. 13), with the 10 and 3 mg/kg/day doses of proanthocyanidin polymer A inhibiting by approximately 10% of the $SaO_2$ decline. It should be noted that in this experiment, therapy ceased on day 6, and by the next day, the $SaO_2$ in the treated animals began to decrease at a rapid rate. This suggests a need to continue therapy a few additional days.

Experiment 2 (Late treatment initiation): The summary results of this experiment are seen in Table 15. It should be noted that in this delayed treatment study all the male toxicity control mice survived the high dose proanthocyanidin polymer A treatment, although they lost considerable weight. These animals were slightly older than those used in Experiment 1, and weighed an average of 1 g more.

As seen in Experiment 1, no significant increase in survivors was seen in the infected, treated groups, although significant mean survival time increases were observed in female mice treated with 10 and 3 mg/kg/day of proanthocyanidin polymer A (Table 15). Overall mean lung scores were again reduced.

The alternate-day lung consolidation findings are shown in FIG. 10. Proanthocyanidin polymer A therapy again caused inhibition of consolidation, although to a lesser extent than seen using earlier-initiated therapy.

Lung virus titers (FIG. 11) were only marginally reduced by proanthocyanidin polymer A therapy.

The $SaO_2$ data for male and female mice are summarized in FIGS. 12 and 13. As was observed in Experiment 1, the female mice tended to respond better to proanthocyanidin polymer A therapy than the males, with somewhat variable, but dose-responsive inhibition of $SaO_2$ decline. We conclude this material has a moderate effect against the murine influenza infection.

In view of amantadine's inactivity, an experiment was run using a 75 mg/kg/day dose of ribavirin, which is known to be highly active against the influenza virus infections (Sidwell, R. W., Huffman, J. H., Hare, G. P., Allen, L. B., Witkowski, J. T., Robins, R., "Broad-Spectrum Antiviral Activity of Virazole: 1-β-D-ribofuranosyl-1,2,4-triazole-3-carboxamide", *Science* 177:705–6 (1972)). The drug was given i.p. twice daily for 5 days beginning 4 hr post-virus inoculation. The same disease parameters as used in the present experiments were employed with the ribavirin study.

The overall results of this ribavirin experiment are shown in Table 16. The drug was not lethally toxic, although it caused moderate host weight loss. All infected, ribavirin-treated mice survived the infection. Lung consolidation and lung virus titers were significantly reduced,and the mean $SaO_2$ decline was inhibited. The lung consolidation, virus titer, and $SaO_2$ data are shown in more detail in FIGS. 14–16.

Thus, in this experiment, ribavirin exerted significant influenza inhibition.

Proanthocyanidin polymer A when given to influenza A (H1N1)-infected mice i.p. once daily for 8 days, exerted moderate inhibition of the infection. The material was most efficacious when treatment was initiated 2 days pre-virus exposure, although significant inhibition was also seen when therapy was delayed until 4 hr post-virus exposure. The toxicity controls did not survive a dose of about 30 mg/kg/day. Disease-inhibiting effects were primarily limited to 10 mg/kg/day. Amantadine was ineffective against this influenza virus strain. Ribavirin was inhibitory to the virus infection. It is concluded that proanthocyanidin polymer A has anti-influenza virus activity.

TABLE 14

Effect of i.p. Treatment with Proanthocyanidin Polymer A on
Influenza A (H1N1) Virus Infections in Mice (Early Treatment Initiation).

Animals: 13–15 g ♂ and ♀ BALB/c Mice.
Virus: Influenza A/NWS/33 virus.
Drug Diluent: Sterile H$_2$O Treatment Schedule: qd × 8, beginning 2 days pre-virus inoculation.
Treatment Route: i.p.
Experiment Duration: 21 Days.

| | | Toxicity controls | | | | Infected, Treated | | | | | | | |
|---|---|---|---|---|---|---|---|---|---|---|---|---|---|
| | Dosage | Surv/Total | | Host Wt. Change$^a$ (g) | | Surv/Total | | MST$^b$ (days) | | Mean Lung | Mean Lung Virus Titer$^c$ | Mean SaO$_2$%$^d$ | |
| Treatment | (mg/kg/day) | ♂ | ♀ | ♂ | ♀ | ♂ | ♀ | ♂ | ♀ | Score$^c$ | (log$_{10}$) | ♂ | ♀ |
| Proanthocyanidin | 30 | 0/3 | 0/3 | — | — | 0/5 | 0/5 | 5.3 | 4.5 | 2.3* | 7.0 | 73.1 | 72.6 |
| Polymer A | 10 | 3/3 | 3/3 | 2.7 | 0.0 | 0/5 | 0/5 | 8.8 | 10.4 | 1.6** | 6.9 | 80.3 | 83.5* |
| | 3 | 3/3 | 3/3 | 3.5 | 1.3 | 0/5 | 0/5 | 8.8 | 8.0 | 2.9 | 6.5 | 80.2 | 83.4* |
| Amantadine | 125 | 3/3 | 3/3 | 2.9 | 0.3 | 0/5 | 0/5 | 9.3 | 9.0 | 2.4 | 6.7 | 79.6 | 78.1 |
| Water | — | — | — | — | — | 0/5 | 0/5 | 10.0 | 9.0 | 3.6 | 6.9 | 82.1 | 80.1 |
| Normals | — | 10/10 | 10/10 | 3.4 | 0.5 | — | — | | | 0.0 | | | |

$^a$Difference between initial weight at start of treatment and weight 18 hr following final treatment of toxicity control mice.
$^b$Mean survival time of mice dying on or before day 21.
$^c$Mean lung scores and virus titers from observations made on days 2, 4, 6, 8. See FIGS. 6 and 7 for comparisons of results of all these time points.
$^d$Mean SaO$_2$% of readings made daily for 11 days. See FIG. 8 for comparisons of daily readings.
*P < 0.05
**P < 0.01

TABLE 15

Effect of i.p. Treatment with Proanthocyanidin Polymer A on
Influenza A (H1N1) Virus Infections in Mice (Early Treatment Initiation).

Animals: 14–16 g ♂ and ♀ BALB/c Mice.
Virus: Influenza A/NWS/33 virus.
Drug Diluent: Sterile H$_2$O Treatment Schedule: qd × 8, beginning 4 hr post-virus inoculation.
Treatment Route: i.p.
Experiment Duration: 21 Days.

| | | Toxicity controls | | | | Infected, Treated | | | | | | | |
|---|---|---|---|---|---|---|---|---|---|---|---|---|---|
| | Dosage | Surv/Total | | Host Wt. Change$^a$ (g) | | Surv/Total | | MST$^b$ (days) | | Mean Lung | Mean Lung Virus Titer$^c$ | Mean SaO$_2$%$^d$ | |
| Compound | (mg/kg/day) | ♂ | ♀ | ♂ | ♀ | ♂ | ♀ | ♂ | ♀ | Score$^c$ | (log$_{10}$) | ♂ | ♀ |
| Proanthocyanidin | 30 | 0/3 | 0/3 | −1.2 | — | 0/5 | 0/5 | 3.6 | 3.4 | 0.4** | 6.3 | 78.1 | 78.4 |
| Polymer A | 10 | 3/3 | 3/3 | 3.8 | 0.4 | 0/5 | 0/5 | 8.4 | 11.2** | 1.5* | 6.4 | 82.8 | 84.1 |
| | 3 | 3/3 | 3/3 | 3.3 | 0.9 | 1/5 | 1/5 | 9.3 | 10.3** | 1.9 | 6.7 | 81.7 | 83.0 |
| Amantadine | 125 | 3/3 | 3/3 | 1.2 | 0.6 | 0/5 | 0/5 | 7.2 | 6.8 | 2.0 | 6.8 | 85.4 | 81.0 |
| Water | — | — | — | — | — | 2/5 | 0/5 | 8.7 | 7.0 | 2.4 | 6.5 | 82.5 | 83.0 |
| Normals | — | 10/10 | 10/10 | 2.8 | 0.0 | — | — | | | 0.0 | | 86.8 | 87.0 |

$^a$Difference between initial weight at start of treatment and weight 18 hr following final treatment of toxicity control mice.
$^b$Mean survival time of mice dying on or before day 21.
$^c$Mean lung scores and virus titers from observations made on days 2, 4, 6, 8. See FIGS. 9 and 10 for comparisons of results of all these time points.
$^d$Mean SaO$_2$% of readings made daily for 11 days. See FIG. 11 for comparisons of daily readings.
*P < 0.05
**P < 0.01

TABLE 16

Effect of i.p. Ribavirin Treatment on Influenza A (H1N1) Virus Infections in Mice.

Animals: 14–16 g ♀ BALB/c Mice.
Virus: Influenza A/NWS/33 virus.
Drug Diluent: Sterile Saline Treatment Schedule: bid × 5 beg.
4 hr post-virus inoculation.
Treatment Route: i.p.
Experiment Duration: 21 Days.

| Compound | Dosage (mg/kg/day) | Toxicity controls | | Infected, Treated | | | | |
|---|---|---|---|---|---|---|---|---|
| | | Surv/ Total | Host Wt. Change[a] (g) | Surv/ Total | MST[b] (days) | Mean Score[c] | Mean Virus Titer[c] ($\log_{10}$) | Mean SaO$_2$%[d] |
| Ribavirin | 75 | 5/5 | 0.6 | 10/10** | >21.0** | 0.3** | 3.9** | 81** |
| Saline | — | — | — | 1/18 | 5.8 | 2.3 | 7.3 | 71 |
| Normals | — | 5/5 | 0.6 | — | — | 0.0 | 0.0 | 88 |

[a]Difference between initial weight at start of treatment and weight 18 hr following final treatment of toxicity control mice.
[b]Mean survival time of mice dying on or before day 21.
[c]Mean lung scores and virus titers from observations made on days 2, 4, 6, 8. See FIGS. 14 and 15 for comparisons of results of all these time points.
[d]Mean SaO$_2$% of readings made daily for 10 days. See FIG. 16 for comparisons of daily readings.
**P < 0.01

10. EFFECTIVENESS OF PROANTHOCYANIDIN POLYMER A FOR TREATMENT OF PARAINFLUENZA VIRUS

Twelve African green monkeys without antibody to parainfluenzavirus, type 3, (PIV-3) were used in an experiment to determine antiviral activity of proanthocyanidin polymer A. The monkeys were divided randomly into four groups of three monkeys each. The respective groups received proanthocyanidin polymer A at doses of 10, 3.3, or 1.0 mg/kg/day with the drug dissolved in 0.5% glucose. A control group of three monkeys received 0.5% glucose without the drug. Each of the monkeys received treatment by intravenous bolus injection as divided doses twice daily at 8 a.m. for 7 days. The injections were made into the saphenous vein of sedated monkeys. See Table 17.

Treatment was initiated four hours before virus inoculation. Four hours later, a $10^{-2}$ dilution of PIV-3 was prepared and inoculated as a 1 ml volume intratracheally and a 1 ml volume placed on the external nares. The titer of the inoculated virus was $10^{3.5}$ TCID$_{50}$ per ml.

Throat swabs were taken daily and placed in 1 ml of tissue culture medium. Fluid was expressed from the swab and the tissue culture fluid was titrated for virus. Tenfold dilutions of the throat swab specimens were prepared and inoculated into duplicate wells of 24 well tissue culture plates seeded with Vero cells. Titers were determined by microscopic examination of the cultures for viral cytopathology. The monkeys were observed daily for clinical symptoms including rhinorrhea, sneezing and coughing. At 14 and 21 days post-infection, blood was drawn for detection of antibody to PIV-3 using a serum neutralization assay.

Each of the 12 monkeys became infected with PIV-3 with the majority shedding virus within 24 hours after virus inoculation. Virus shedding continued in all monkeys through the eighth day post-infection with some monkeys shedding virus through day 9 and 10. See Table 18.

The mean virus titers for each group are shown in Table 19. Proanthocyanidin polymer A at 10 mg/kg/day appear to reduce the mean titers on all of the days post-infection by one log or better. The 3.3 mg/kg/day dose was seen to have a slightly lesser effect than the 10 mg/kg/day dose but again all titers were less than the controls. No appreciable effect was seen at 1.0 mg/kg/day.

Symptoms of respiratory infection were more common in the control monkeys than in any one of the three proanthocyanidin polymer A treated groups. During the 11 days of observation with 3 monkeys per group, 33 total symptom days are possible. In the group receiving proanthocyanidin polymer A at 10 mg/kg/day only 7 of those 33 days were observed to have monkeys with symptoms. The 3.3 mg/kg/day dose resulted in only 2 days and the 1.0 mg/kg/dose resulted in 7 days. The principal symptom observed was rhinorrhea (See Table 20).

Antibody titers to PIV-3 at 14 and 21 days after virus inoculation are reported. All monkeys were observed to develop antibody with what appeared to be slightly higher titers in the treated monkeys when compared with the untreated controls. See Table 21.

Thus, proanthocyanidin polymer A was seen to have a beneficial effect on the course of parainfluenzavirus, type 3, in African green monkeys treated with 10 and 3.3 mg/kg/day with proanthocyanidin polymer A. Proanthocyanidin polymer A was seen to reduce the titers of virus shed in the throats of infected monkeys and may have reduced the symptoms seen with this infection.

TABLE 17

Treatment Groups of African Green Monkeys Selected to Evaluate the Antiviral Activity of Proanthocyanidin Polymer A* Against Parainfluenzavirus, Type 3

| Monkey Number | Sex | Weight (kg) | Treatment with *P. Pol. A |
|---|---|---|---|
| L299 | F | 2.0 | 5 mg/kg, b.i.d., i.v. |
| L341 | M | 4.6 | 5 mg/kg, b.i.d., i.v. |
| L300 | M | 1.8 | 5 mg/kg, b.i.d., i.v. |
| K144 | M | 5.0 | 1.67 mg/kg, b.i.d., i.v |
| L302 | M | 2.4 | 1.67 mg/kg, b.i.d., i.v |
| K143 | M | 4.6 | 1.67 mg/kg, b.i.d., i.v |
| L301 | M | 2.8 | 0.5 mg/kg, b.i.d., i.v. |
| K347 | M | 4.8 | 0.5 mg/kg, b.i.d., i.v. |
| K342 | F | 2.8 | 0.5 mg/kg, b.i.d., i.v. |
| K337 | F | 2.8 | 0.5% glucose, b.i.d, iv |
| K346 | F | 3.0 | 0.5% glucose, b.i.d, iv |
| K345 | F | 3.2 | 0.5% glucose, b.i.d, iv |

TABLE 18

Effect of Proanthocyanidin Polymer A* Treatment Upon Virus Shedding
From African Green Monkeys Infected With Parainfluenzavirus, Type 3

| Treatment | Monkey Number | Log of Virus Titer on Days Post-Infection | | | | | | | | | |
|---|---|---|---|---|---|---|---|---|---|---|---|
| | | 1 | 2 | 3 | 4 | 5 | 6 | 7 | 8 | 9 | 10 |
| Control | K337 | 1.0 | 4.0 | 5.0 | 5.0 | 6.0 | 5.0 | 4.0 | 3.0 | 1.5 | 1.0 |
| 0.5% | K346 | 2.0 | 3.5 | 5.0 | 4.5 | 5.5 | 6.0 | 5.0 | 4.0 | 2.0 | 1.0 |
| glucose iv. | K345 | 2.0 | 3.0 | 4.5 | 4.5 | 6.0 | 5.0 | 5.0 | 3.0 | 1.0 | <1.0 |
| *P. Pol. A; | L299 | 1.0 | 2.0 | 3.0 | 4.0 | 4.0 | 5.0 | 2.5 | 1.5 | <1.0 | <1.0 |
| 10 mg/kg/dy | K341 | <1.0 | 2.0 | 3.0 | 4.5 | 3.0 | 3.5 | 3.0 | 2.0 | 1.5 | <1.0 |
| i.v., BID | L300 | 1.0 | 2.0 | 3.0 | 4.0 | 3.5 | 4.0 | 3.0 | 1.0 | <1.0 | <1.0 |
| *P. Pol. A; | K144 | <1.0 | 1.0 | 3.0 | 4.0 | 4.0 | 4.5 | 5.0 | 4.0 | 2.0 | 1.0 |
| 3.3 mg/kg/dy | L302 | 2.0 | 3.0 | 2.0 | 4.5 | 4.0 | 5.0 | 3.5 | 3.0 | 1.0 | <1.0 |
| i.v., BID | K143 | 1.0 | 3.0 | 2.5 | 3.5 | 4.5 | 5.0 | 3.5 | 2.0 | 1.0 | <1.0 |
| *P. Pol. A; | L301 | 2.0 | 4.0 | 4.5 | 5.0 | 4.5 | 4.5 | 3.5 | 2.0 | 1.0 | <1.0 |
| 1.0 mg/kg/dy | K347 | 2.0 | 3.0 | 3.0 | 5.0 | 5.0 | 6.0 | 4.0 | 1.0 | <1.0 | <1.0 |
| i.v., BID | K342 | 2.0 | 3.0 | 4.5 | 5.0 | 5.0 | 6.0 | 5.0 | 3.0 | 1.5 | 1.0 |

TABLE 19

Mean Daily Titers of Parainfluenzavirus, Type 3 in
African Green Monkeys Treated With
Proanthocyanidin Polymer A

| Treatment | Mean Log of Virus Titer on Days Post-Infection | | | | | | | | | |
|---|---|---|---|---|---|---|---|---|---|---|
| | 1 | 2 | 3 | 4 | 5 | 6 | 7 | 8 | 9 | 10 |
| Glucose Control | 1.7 | 3.5 | 4.8 | 4.7 | 5.8 | 5.5 | 4.7 | 3.3 | 1.5 | 0.7 |
| *P. Polymer A; 10 mg/kg/day | 0.7 | 2.0 | 3.0 | 4.2 | 3.5 | 4.2 | 2.8 | 1.5 | 0.5 | <1.0 |
| *P. Polymer A; 3.3 mg/kg/day | 1.0 | 2.3 | 2.5 | 4.0 | 4.2 | 4.8 | 4.0 | 3.0 | 1.3 | 0.3 |
| *P. Polymer A; 1.0 mg/kg/day | 2.0 | 3.3 | 4.0 | 5.0 | 4.8 | 5.5 | 4.2 | 2.0 | 0.8 | 0.3 |

TABLE 20

Total Days in Which Monkeys Showed Symptoms
to Parainfluenzavirus, Type 3 Infection

| Treatment | Symptom Days/Total |
|---|---|
| Control, glucose | 13/33 |
| P. Pol. A, 10 mg/kg/day | 7/33 |
| P. Pol. A, 3.3 mg/kg/day | 2/33 |
| P. Pol. A, 1.0 mg/kg/day | 7/33 |

TABLE 21

Antibody Titers to Parainfluenzavirus, Type 3,
in African Green Monkeys Infected With the Virus
and Treated With Proanthocyanidin Polymer A*

| Treatment | Monkey Number | Antibody Titer at Days P.I. | |
|---|---|---|---|
| | | 14 Days | 21 Days |
| Control | K337 | 1:40 | 1:160 |
| 0.5% | K346 | 1:20 | 1:80 |
| glucose, i.v. | K345 | 1:80 | 1:160 |
| *P. Polymer A, | L299 | 1:160 | 1:320 |
| 10 mg/kg/day, | K341 | 1:160 | 1:320 |
| i.v. | L300 | 1:160 | 1:320 |
| *P. Polymer A, | K144 | 1:80 | 1:80 |
| 3.3 mg/kg/day, | L302 | 1:160 | 1:320 |
| i.v. | K143 | 1:160 | 1:160 |
| *P. Polymer A, | L301 | 1:160 | 1:320 |
| 1.0 mg/kg/day | K347 | 1:80 | 1:160 |

TABLE 21-continued

Antibody Titers to Parainfluenzavirus, Type 3,
in African Green Monkeys Infected With the Virus
and Treated With Proanthocyanidin Polymer A*

| Treatment | Monkey Number | Antibody Titer at Days P.I. | |
|---|---|---|---|
| | | 14 Days | 21 Days |
| i.v. | K342 | 1:40 | 1:180 |

10.1 EFFECTIVENESS OF PROANTHOCYANIDIN POLYMER A FOR TREATMENT OF HERPES SIMPLEX VIRUS TYPE 2 VAGINITIS

In vivo experiments were performed to study the effectiveness of proanthocyanidin polymer A in comparison with ganciclovir against herpes simplex virus type 2. Ganciclovir is known to be effective against herpes simplex virus type 2.

In one series of experiments, both compositions were formulated for intraperitoneal injection by dissolving in physiological saline.

Swiss Webster female mice (Simonsen Labs, Gilroy, Calif.) weighing approximately 20 grams each at the start of the experiment were infected intravaginally with herpes simplex virus type 2 (HSV-2), E194 strain. This was accomplished in a 3-step process. First, the vagina of each mouse was swabbed for 5 seconds with a cotton tip applicator dipped in 0.1N NaOH. This treatment irritates the vaginal area so that the infection takes better. Approximately 1 hour later each vagina was dry swabbed for 5 seconds. Then an applicator dipped in virus medium was used to swab each mouse for 20 seconds. The swabs were gently and slowly twisted back and forth during the time they were in place.

Six hours after virus infection, intraperitoneal (i.p.) injections were administered using proanthocyanidin polymer A, ganciclovir, or placebo. Treatments were also given i.p. twice daily on days 1 through 7 after virus challenge. The daily dose of each compound was 30 mg/kg/day, with 15 mg/kg given at each injection. Since on day 0 of the infection only one dose was given, the daily dose for that day was 15 mg/kg/day.

Groups of 5 mice were sham-infected using the process described above for virus infection, except that no virus was present for the final step. These mice were treated the same way and at the same times as above. Mice were checked daily for survival, and weights were recorded before the first (day 0) and after the last (day 8) treatment.

Lesion scores in infected mice were determined daily on days 3–14 of the infection. A score of 1+ indicates redness immediately around the vagina. 2+ indicates spread of the lesion toward the anus. 3+ indicates a lesion (usually with swelling) from the vagina to the anus. There are variations to this since some mice may have a vaginal lesion plus a lesion on the tail. Because many of the mice go on to die, the lesion score near the time of death is carried through to the end of the 14 days. If this were not done, lesion scores in the placebo group would appear to go down as the most affected mice die off. Some animals developed hind limb paralysis (and later died). This condition did not add to the lesion score.

Deaths were recorded daily for 21 days. The mean day of death calculation took into account only mice that died. Vaginal virus titers were made by titration of virus obtained from vaginal swabs 3 days after virus inoculation. These titrations were conducted in Vero cells in 96-well plates. Calculation of virus titer was made by the 50% endpoint dilution method of Reed, L. J. and Meunch, M., *Am. J. Hyg.*, 27:493–498 (1938).

Statistical interpretations of survival (Fisher exact test), mean day to death (Student's t test) and virus titer (Student's t test) were made by two-tailed analyses.

Table 22 below shows the average lesion scores with standard deviations and statistical analyses for the experiment.

TABLE 22

Effect of Intraperitoneal Proanthocyanidin Polymer A Treatment on Herpes Simplex Virus Type 2 (HSV-2) Vaginitis in Mice.

| | Average Lesion Score | | |
|---|---|---|---|
| Day[a] | Proanth. Pol. A (30 mg/kg/day) | Ganciclovir (30 mg/kg/day) | Placebo |
| 3 | 0.2 ± 0.2[b] | 0.1 ± 0.2 | 0.3 ± 0.3 |
| 4 | 0.2 ± 0.3 | 0.2 ± 0.2** | 1.1 ± 1.0 |
| 5 | 0.7 ± 0.9** | 0.2 ± 0.2** | 1.9 ± 1.2 |
| 6 | 1.3 ± 1.4** | 0.2 ± 0.2*** | 3.1 ± 1.4 |
| 7 | 1.5 ± 1.3** | 0.2 ± 0.2*** | 3.1 ± 1.6 |
| 8 | 1.8 ± 1.5* | 0.3 ± 0.4*** | 3.0 ± 1.6 |
| 9 | 2.1 ± 1.4 | 0.4 ± 0.3*** | 3.2 ± 1.4 |
| 10 | 2.3 ± 1.4 | 0.5 ± 0.5*** | 3.2 ± 1.3 |
| 11 | 2.3 ± 1.5 | 0.5 ± −.4*** | 3.2 ± 1.3 |
| 12 | 2.2 ± 1.4 | 0.9 ± 0.2*** | 3.2 ± 1.3 |
| 13 | 1.8 ± 1.5* | 0.6 ± 0.6*** | 3.2 ± 1.4 |
| 14 | 1.8 ± 1.5* | 0.6 ± 0.6*** | 3.1 ± 1.4 |
| Grand Avg. (Days 3–14) | 1.5 ± 0.8** | 0.4 ± 0.2*** | 2.6 ± 1.0 |

[a]After virus challenge.
[b]Standard deviation.
*p < 0.05,
**p < 0.01
***p < 0.001 (two-tailed Student's t test).

Figure 17:
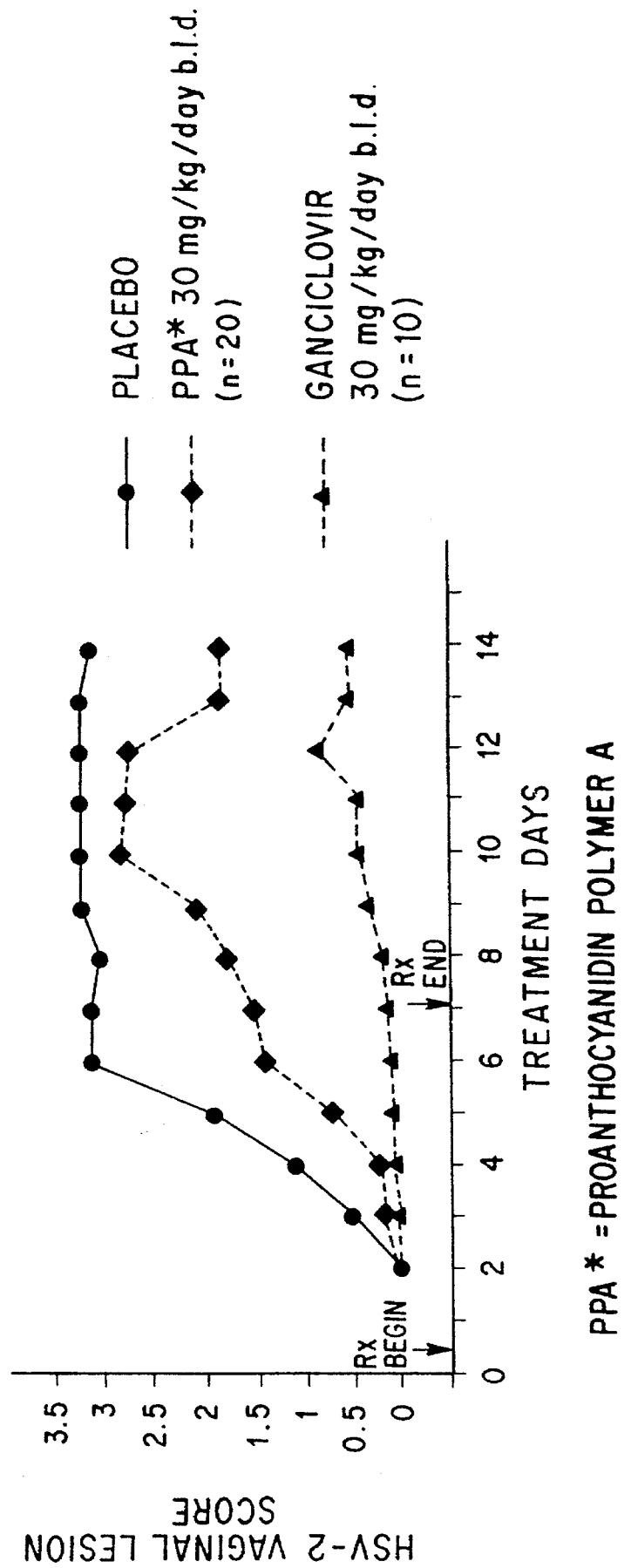

Proanthocyanidin polymer A showed a statistically significant decrease in average lesion score compared to the placebo control. Ganciclovir was also effective. FIG. 17 gives a visual impression of the degree of lesion inhibition exhibited by 30 mg proanthocyanidin polymer A per kg relative to the placebo control and ganciclovir. Table 23 shows survival of the treated mice.

TABLE 23

Effect of Intraperitoneal Proanthocyanidin Polymer A Treatment on Survival and Vaginal Virus Titer in Mice Infected Intravaginally with Herpes Simplex Virus Type 2 (HSV-2).

| Compound | Dose | Survivors/ Total (%) | Mean Day to Death | Virus Titer[a] (Day 3) | Host Wt. Change[c] |
|---|---|---|---|---|---|
| | | Virus-Infected | | | |
| Pro. Pol. A | 30 | 4/10(40) | 9.5 ± 3.2 | 2.9 ± 1.1 | |
| Ganciclovir | 30 | 10/10(100)** | >21 | 1.7 ± 1.0* | |
| Placebo | — | 3/20(15) | 8.2 ± 2.9 | 3.8 ± 1.2 | |
| | | Uninfected Toxicity Controls | | | |
| Pro. Pol. A | 30 | 5/5(100) | >21 | | +2.8 |
| Ganciclovir | 30 | 5/5(100) | >21 | | +1.0 |
| Placebo | — | 5/5(100) | >21 | | +2.5 |

[a]Log$_{10}$ 50% cell culture infectious dose per ml.
[b]Determined on day 8. Represents the difference in grams between day 0 and day 8 weights.
*P < 0.002, two-tailed Fisher exact test (survival) or two-tailed Student's t test (mean day to death and virus titer parameters.)

Proanthocyanidin polymer A showed an increased survival (40% survival compared to 15% in the placebo group). The ganciclovir group had 100% survival. Table 23 also shows that proanthocyanidin polymer A treated mice had less virus than the placebo control, but the results were not statistically significant. Ganciclovir caused a significant reduction in virus titer.

Results in toxicity control mice showed proanthocyanidin polymer A was well tolerated and caused no adverse effects at the doses used. Ganciclovir treated mice gained less weight than placebo controls.

Thus, proanthocyanidin polymer A administered intraperitoneally at a dose of 30 mg/kg/day had moderate antiviral activity in this model. There was no apparent toxicity of the proanthocyanidin polymer A formulation to mice.

Another series of preliminary experiments, in which the proanthocyanidin polymer A composition is administered orally, showed some anti-HSV-2 activity but only at the highest dose administered, i.e., 270 mg/kg/day.

In another series of experiments, the proanthocyanidin polymer A composition was formulated for topical application against HSV-2. The efficacy of proanthocyanidin polymer A is compared with ganciclovir and acyclovir. Both ganciclovir powdre and acyclovir cream were obtained commercially. Squibb cream base #8, which served as a vehicle and as the topical placebo control, was also commercially obtained.

The methods of infecting the mice, setting toxicity control and the parameters measured to evaluate the infection were the same as described above for the intraperitoneal tests. Topical treatments on the day of infection were given at +6 hours. They were then given twice daily for 7 more days.

Figure 18:
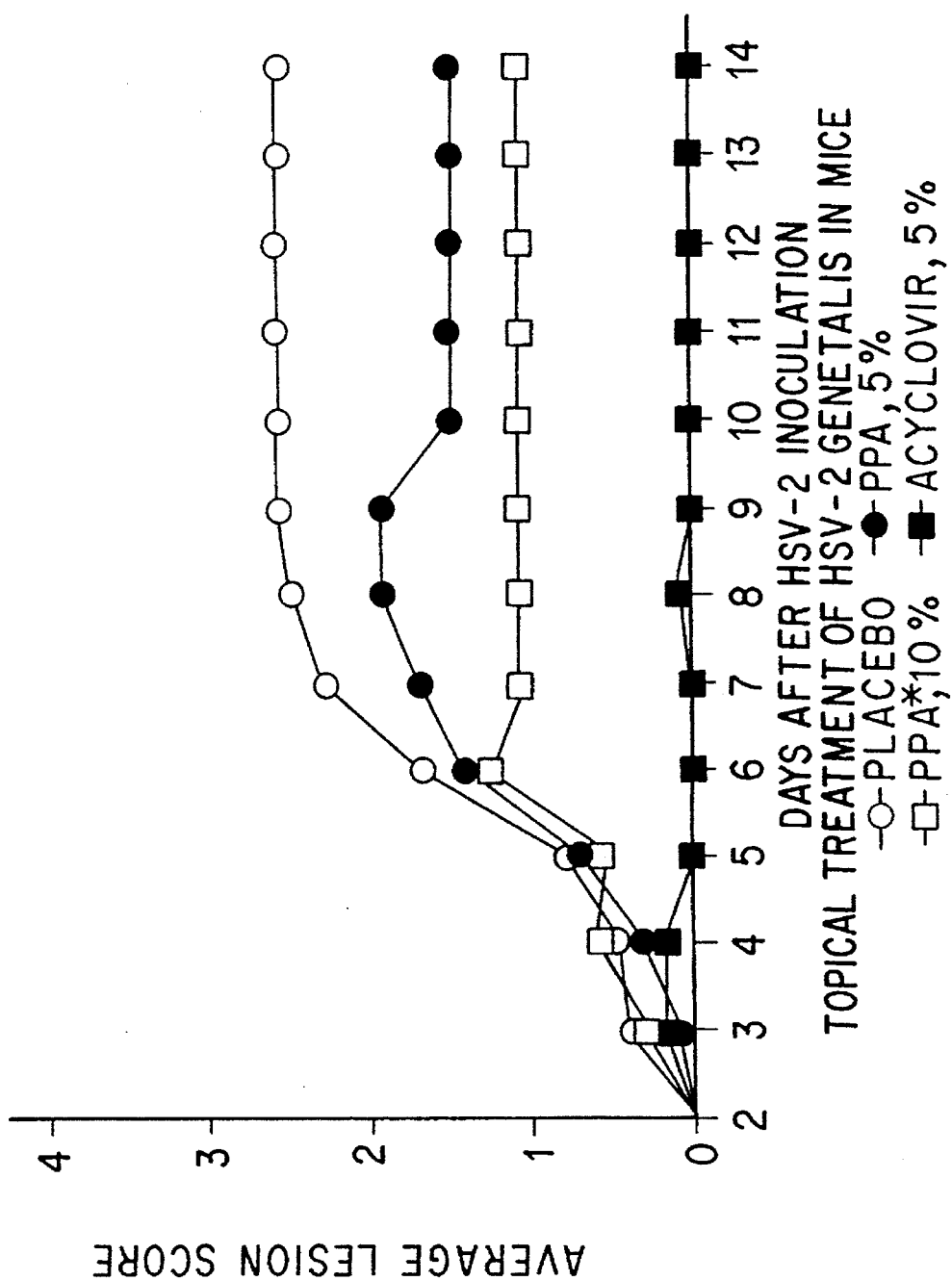

Treatment for 7.5 days with proanthocyanidin polymer A at two doses resulted in a statistically significant reduction in lesion scores of the period of evaluation for the 10% dose. This is presented graphically in FIG. 18 and in Table 24. The 5% dose also reduced lesion development relative to the placebo control, but the results were not statistically significant. Acyclovir cream nearly completely prevented lesion formation in infected animals. More mice treated with proanthcyanidin polymer A at 5% and 10% doses survived the infection that placebo controls (Table 25) and vaginal virus titers were reduced at the 10% dose. In addition, the numbers of mice without lesions on day 14 were greater than in the placebo group. None of the uninfected toxicity control mice lost weight or died as a result of treatment with any of the cream formulations. (Table 25).

It can be concluded that topically applied proanthocyanidin polymer A as a 10% cream was active. Only three mice developed vaginal lesions, but the lesions all progressed to maximum severity. The proanthocyanidin polymer A cream formulations were somewhat dry to the touch, since the composition hydrated and absorbed some of the water from the Squibb cream base. This may have affected the performance of the proanthocyanidin polymer A cream. Partial hydration of the material in water prior to mixing it with the cream base may provide a more aqueous and bioavailable product for topical application.

TABLE 24

Effect of topical Proanthocyanidin Polymer A Treatment on Herpes Simplex Virus Type 2 (HSV-2) Vaginitis in mice.

| | Average Lesion Score | | | |
|---|---|---|---|---|
| Day[a] | P. Pol. A 5% | P. Pol. A 10% | Acyclovir 5% | Placebo |
| 3 | $0.3 \pm 0.3^b$ | $0.2 \pm 0.3$ | $0.2 \pm 0.2$ | $0.3 \pm 0.3$ |
| 4 | $0.3 \pm 0.5$ | $0.6 \pm 1.0$ | $0.1 \pm 0.2$ | $0.5 \pm 0.9$ |
| 5 | $0.7 \pm 1.1$ | $0.6 \pm 1.1$ | $0.0 \pm 0.0$*** | $0.8 \pm 0.9$ |
| 6 | $1.0 \pm 1.6$ | $1.3 \pm 1.7$ | $0.0 \pm 0.0$*** | $1.7 \pm 1.5$ |
| 7 | $1.7 \pm 1.8$ | $1.1 \pm 1.8$ | $0.0 \pm 0.0$*** | $2.3 \pm 1.7$ |
| 8 | $1.9 \pm 2.0$ | $1.1 \pm 1.8$ | $0.1 \pm 0.2$*** | $2.5 \pm 1.8$ |
| 9 | $1.9 \pm 1.8$ | $1.1 \pm 1.8$ | $0.0 \pm 0.0$*** | $2.6 \pm 1.8$ |
| 10 | $1.6 \pm 1.1$ | $1.1 \pm 1.8$ | $0.0 \pm 0.0$*** | $2.6 \pm 1.8$ |
| 11 | $1.6 \pm 1.1$ | $1.1 \pm 1.8$ | $0.0 \pm 0.0$*** | $2.6 \pm 1.8$ |
| 12 | $1.6 \pm 1.1$ | $1.1 \pm 1.8$ | $0.0 \pm 0.0$*** | $2.6 \pm 1.8$ |
| 13 | $1.6 \pm 1.1$ | $1.1 \pm 1.8$ | $0.0 \pm 0.0$*** | $2.6 \pm 1.8$ |
| 14 | $1.6 \pm 1.1$ | $1.1 \pm 1.8$ | $0.0 \pm 0.0$*** | $2.6 \pm 1.8$ |
| Grnd Avg (Days 3–14) | $1.4 \pm 0.6$ | $1.0 \pm 0.3$** | $0.1 \pm 0.1$*** | $2.0 \pm 0.9$ |

[a]After virus challenge.
[b]Standard deviation.
*$p < 0.05$,
**$p < 0.01$,
***$p < 0.001$ (two-tailed Student's t test).

TABLE 25

Effect of Topical Proanthocyanidin Polymer A Treatment on Survival, Vaginal Virus Titers, and Numbers Without Lesions on Mice Infected Intravaginally with Herpes Simplex Virus Type 2 (HSV-2).

| Compound | Dose[a] | Survivors/ Total (%) | Mean Day to Death | Virus Titer[b] (Day 2) | No. of Mi W/O Lesio | Host Wt. Ch |
|---|---|---|---|---|---|---|
| | | | Virus-Infected | | | |
| Placebo | — | 6/20 (30) | $9.6 \pm 2.6^d$ | $2.8 \pm 2.2$ | 6/20 | |

TABLE 25-continued

Effect of Topical Proanthocyanidin Polymer A Treatment on
Survival, Vaginal Virus Titers, and Numbers Without Lesions on
Mice Infected Intravaginally with Herpes Simplex Virus Type 2 (HSV-2).

| Compound | Dose[a] | Survivors/ Total (%) | Mean Day to Death | Virus Titer[b] (Day 2) | No. of Mi W/O Lesio | Host Wt. Ch |
|---|---|---|---|---|---|---|
| Acyclovir | 5 | 10/10 (100)* | >21 | 0.6 ± 0.2* | 10/10 | |
| P. Poly A | 5 | 5/10 (50) | 9.4 ± 1.1 | 2.6 ± 2.5 | 5/10 | |
| *P. Poly A | 10 | 7/10 (70) | 7.7 ± 1.5 | 1.3 ± 1.2 | 7/10 | |
| Uninfected Toxicity Controls | | | | | | |
| Placebo | — | 5/5 (100) | >21 | | | +1.3 |
| Acyclovir | 5 | 5/5 (100) | >21 | | | +2.0 |
| P. Poly A | 10 | 5/5 (100) | >21 | | | +1.6 |

[a]Percent of compound in a polyethylene glycol cream base.
[b]$Log_{10}$ 50% cell culture infectious dose per ml.
[c]On day 14 of the infection.
[d]Standard deviation.
[e]Determined on day 8. Represents the difference in grams between day 0 and day 8 weigh
*P < 0.05, two-tailed Fisher exact test (survival and numbers without lesions) or two-tai Student's t test (mean day to death and virus titer parameters).

11. EFFECTIVENESS OF PROANTHOCYANIDIN POLYMER B FOR TREATMENT OF RSV

Results from in vitro tests for RSV antiviral activity, performed under the same procedures as the tests with proanthocyanidin polymer A, indicate that proanthocyanidin polymer B is effective and has an $ED_{50}$ of 6 µg/ml.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method of treating a virus infection comprising administering to a warm-blooded animal an effective amount of an antiviral agent comprising a proanthocyanidin polymer, which polymer is obtained from a Croton species and is characterized by:
   (a) the capability of dissolving in water and/or an aqueous solution;
   (b) the capability of exerting a pronounced antiviral effect when administered in vivo to an animal or a human;
   (c) having a structure comprising flavonoid units selected from the group consisting of catechins, epicathechins, gallocatechins, galloepicatechins and combinations thereof; and
   (d) $^{13}C$ NMR spectra having peak position at δ154.2, 145.1, 143.7, 132.8, 131.2, 130.3, 120.9–118.6 (series of broad peaks), 116.1, 115.4, 114.3, 108.0, 106.3, 96.6, 95.3, 81.8, 77.6, 75.3, 72.6, 71.5, 65.6, 37.1, 35.3, and 27.7.

2. The method of claims 1 in which the proanthocyanidin polymer has 2 to 11 flavonoid units.

3. The method of claim 1 in which the proanthocyanidin polymer has an average of 7 flavonoid units.

4. The method of claim 1 in which the virus is a paramyxovaridae, orthomyxovaridae or herpes virus.

5. A method of treating a respiratory virus infection, comprising administering to a warm-blooded animal an effective amount of an antiviral agent comprising a proanthocyanidin polymer which polymer is obtained from a Croton species and is characterized by:
   (a) the capability of dissolving in water and/or an aqueous solution;
   (b) the capability of exerting a pronounced antiviral effect when administered in vivo to an animal or a human;
   (c) having a structure comprising flavonoid units selected from the group consisting of catechins, epicathechins, gallocatechins, galloepicatechins and combinations thereof; and
   (d) $^{13}C$ NMR spectra having peak position at δ154.2, 145.1, 143.7, 132.8, 131.2, 130.3, 120.9–118.6 (series of broad peaks), 116.1, 115.4, 114.3, 108.0, 106.3, 96.6, 95.3, 81.8, 77.6, 75.3, 72.6, 71.5, 65.6, 37.1, 35.3, and 27.7.

6. The method of claim 5 in which the proanthocyanidin polymer has 2 to 11 flavonoid units.

7. The method of claim 5 in which the proanthocyanidin polymer has an average of 7 flavonoid units.

8. The method of claim 5 in which the respiratory virus is a respiratory syncytial virus.

9. The method of claim 5 in which the respiratory virus is Parainfluenza virus 3, Influenza A virus, Influenza B virus, or a virus associated with otitis media or otitis externa.

10. The method according to claim 1 or 5 wherein the proanthocyanidin polymer is administered intravenously.

11. The method according to claim 1 or 5 wherein the proanthocyanidin polymer is administered intraperitoneally.

12. The method according to claim 1 or 5 wherein the proanthocyanidin polymer is administered subcutaneously.

13. The method according to claim 1 or 5 wherein the proanthocyanidin polymer is administered intramuscularly.

14. The method according to claim 1 or 5 wherein the proanthocyanidin polymer is administered orally.

15. The method according to claim 1 or 5 wherein the proanthocyanidin polymer is administered topically.

16. The method according to claim 1 or 5 wherein the proanthocyanidin polymer is administered by aerosol.

17. The method according to claim 11 wherein the proanthocyanidin polymer is administered intraperitoneally in a range of 0.1 to 10 mg/kg.

18. The method according to claim 14 wherein the proanthocyanidin polymer is administered orally in a range of 5.0 to 30 mg/kg.

19. The method according to claim 16 wherein the proanthocyanidin polymer is administered in a range of 5 to 30 mg/kg/day.

20. A method for treating a respiratory syncytial virus infection, comprising administering, to a warm-blooded animal, an effective amount of an antiviral agent comprising a proanthocyanidin polymer wherein said proanthocyanidin polymer is obtained from a Croton tree by a method which comprises:

(a) extracting the whole plant, the bark, the stems, the roots or the latex of the Croton tree with a lower alcohol of about 1–3 carbons, acetone, water or other water miscible solvent or combinations thereof to obtain an aqueous soluble fraction;

(b) subjecting the aqueous soluble fraction to gel filtration using water and/or water and a water miscible solvent with or without a buffer as the mobile phase; or to reversed-phase column chromatography using water, and/or water and a water miscible solvent as the mobile-phase; or to gel permeation chromatography using water and/or water and water miscible solvent and acetonitrile with or without a buffer as the mobile phase, or combination thereof; and (c) collecting the fractions detectable by ultraviolet spectroscopy having a λ maximum at about 200–350 nm, wherein the collected fraction is characterized by:

(i) the capability of dissolving in water and/or an aqueous solution;

(ii) the capability of exerting a pronounced antiviral effect when administered in vivo to an animal or a human;

(iii) having a structure comprising flavonoid units selected from the group consisting of catechins, epicathechins, gallocatechins, galloepicatechins and combinations thereof; and (iv) $^{13}$C NMR spectra having peak position at δ154.2, 145.1, 143.7, 132.8, 131.2, 130.3, 120.9–118.6 (series of broad peaks), 116.1, 115.4, 114.3, 108.0, 106.3, 96.6, 95.3, 81.8, 77.6, 75.3, 72.6, 71.5, 65.6, 37.1, 35.3, and 27.7.

21. The method of claim 20 in which the Croton tree is Croton lechleri.

22. The method of claim 20 in which the proanthocyanidin polymer is administered parenterally at a dose range of 0.1–10 mg/kg body weight, orally at a dose range of 5.0–30.0 mg/kg body weight, or by inhalation at a dose range of 5–30 mg/kg/day.

* * * * *